US 6,656,174 B1

(12) United States Patent
Hegde et al.

(10) Patent No.: US 6,656,174 B1
(45) Date of Patent: Dec. 2, 2003

(54) DEVICES AND METHODS FOR CREATING LESIONS IN BLOOD VESSELS WITHOUT OBSTRUCTING BLOOD FLOW

(75) Inventors: Anant V. Hegde, Newark, CA (US); Steven L. Olson, Hollister, CA (US); David K. Swanson, Campbell, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 133 days.

(21) Appl. No.: 09/619,857

(22) Filed: Jul. 20, 2000

(51) Int. Cl.⁷ .......................... A61B 18/08; A61B 18/14
(52) U.S. Cl. .......................... 606/41; 606/45; 606/159; 607/122
(58) Field of Search .............................. 606/41, 44, 45, 606/46, 47, 159, 167, 170; 607/113, 99, 122, 123

(56) References Cited

U.S. PATENT DOCUMENTS

| | | | |
|---|---|---|---|
| 4,798,586 A | * | 1/1989 | Stevens .................. 604/96 |
| 5,345,936 A | * | 9/1994 | Pomeranz et al. ......... 607/122 |
| 5,471,982 A | | 12/1995 | Edwards et al. |
| 5,575,810 A | | 11/1996 | Swanson et al. |
| 5,722,403 A | | 3/1998 | McGee et al. |
| 5,797,903 A | | 8/1998 | Swanson et al. |
| 5,846,238 A | | 12/1998 | Jackson et al. |
| 5,846,239 A | | 12/1998 | Swanson et al. |
| 5,911,739 A | | 6/1999 | Kordis et al. |
| 5,919,200 A | * | 7/1999 | Stambaugh et al. ........ 606/159 |
| 5,925,038 A | | 7/1999 | Panescu et al. |
| 5,961,513 A | | 10/1999 | Swanson et al. |
| 6,012,457 A | | 1/2000 | Lesh |
| 6,024,740 A | | 2/2000 | Lesh et al. |
| 6,076,012 A | | 6/2000 | Swanson et al. |
| 6,142,993 A | | 11/2000 | Whayne et al. |
| 6,210,408 B1 | * | 4/2001 | Chandrasekaran et al. ..... 606/41 |
| 6,230,060 B1 | * | 5/2001 | Mawhinney ................ 607/101 |
| 6,251,109 B1 | * | 6/2001 | Hassett et al. ............. 606/45 |

FOREIGN PATENT DOCUMENTS

| | | |
|---|---|---|
| WO | WO 00/51511 | 9/2000 |
| WO | WO 00/67656 | 11/2000 |
| WO | WO 01/37723 A2 | 5/2001 |

OTHER PUBLICATIONS

Application Ser. No. 08/984,414; Koblish et al.; filed Dec. 3, 1997; Group Art Unit No. 3739.

* cited by examiner

Primary Examiner—Philip H. Leung
(74) Attorney, Agent, or Firm—Bingham McCutchen LLP

(57) ABSTRACT

An ablation catheter that includes radially disposed inflatable chambers is provided. The ablation catheter includes an elongate catheter body and an electrode structure mounted on the distal end of the catheter body. The electrode structure includes a plurality of radially disposed inflatable chambers. The elongate catheter body may be composed of an inner shaft having an inner shaft lumen, a stiffening mandrel disposed within the inner shaft lumen, and an outer shaft having an outer shaft lumen, wherein the inner shaft is disposed within the outer shaft lumen. The outer shaft includes a plurality of inflation lumens in communication with the interior regions of the inflatable chambers, which deliver an inflation medium to the inflatable chambers. The inner shaft includes a plurality of lumens that house electrical leads for delivering ablation energy to the electrode structure.

48 Claims, 20 Drawing Sheets

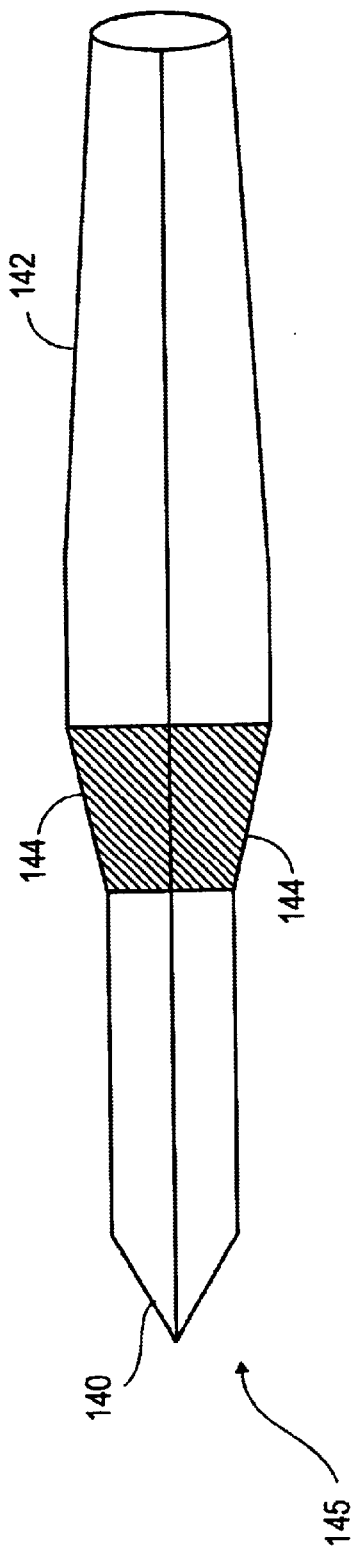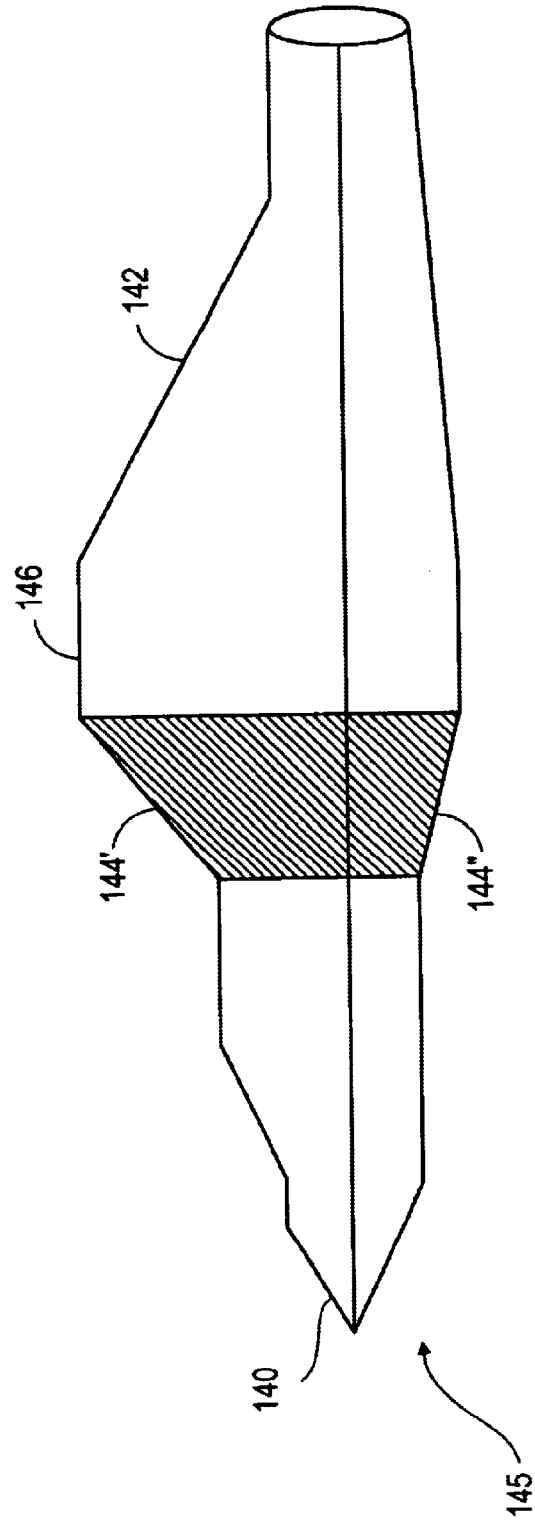
FIGURE 15A
FIGURE 15B

DEVICES AND METHODS FOR CREATING LESIONS IN BLOOD VESSELS WITHOUT OBSTRUCTING BLOOD FLOW

FIELD OF THE INVENTION

The present invention pertains to the field of catheter systems, and more particularly, to therapeutic catheters for the electrophysiological treatment of cardiac rhythm disturbances.

BACKGROUND OF THE INVENTION

Normal sinus rhythm of the heart begins with the sinoatrial node (or "SA node") generating a depolarization wave front, or electrical impulse. This impulse causes adjacent myocardial tissue cells in the right and left atria to depolarize. The electrical impulse uniformly propagates across the right and left atria and the atrial septum to the atrioventricular node (or "AV node"), causing the atria to contract and empty blood from the atria into the ventricles. The electrical impulse propagates through the AV node to the atrioventricular bundle (or "HIS bundle"), where it further propagates across the ventricles, causing the ventricles to contract. The AV node regulates the propagation delay to the HIS bundle, so that atrial systole occurs during ventricular diastole. This coordination of the electrical activity results in the described, organized sequence of myocardial contraction leading to a normal heartbeat.

Sometimes aberrant conductive pathways develop in heart tissue, which disrupt the normal path of depolarization events. For example, anatomical obstacles, called "conduction blocks," can cause the electrical impulse to degenerate into several circular wavelets that circulate about the obstacles. These wavelets, called "reentry circuits," disrupt the normal activation of the atria or ventricles. As a further example, localized regions of ischemic myocardial tissue may propagate depolarization events slower than normal myocardial tissue. The ischemic region, also called a "slow conduction zone," creates the substrate for errant, circular propagation patterns, called "circus motion." The circus motion also disrupts the normal depolarization patterns, thereby disrupting the normal contraction of the heart tissue.

The aberrant conductive pathways create abnormal, irregular, and sometimes life-threatening heart rhythms, called arrhythmias. An arrhythmia can take place in the atria, for example, as in atrial tachycardia (AT) or atrial flutter (AF). The arrhythmia can also take place in the ventricle, for example, as in ventricular tachycardia (VT). In treating arrhythmias, it is sometimes essential that the location of the sources of the aberrant pathways (called focal arrhythmia substrates) be located. Once located, the focal arrhythmia substrate can be destroyed, or ablated, e.g., by surgical cutting, or the application of heat. In particular, ablation can remove the aberrant conductive pathway, thereby restoring normal myocardial contraction. An example of such an ablation procedure is described in U.S. Pat. No. 5,471,982, issued to Edwards et al.

Alternatively, arrhythmias may be treated by actively interrupting all of the potential pathways for atrial reentry circuits by creating complex lesion patterns on the myocardial tissue. An example of such a procedure is described in U.S. Pat. No. 5,575,810, issued to Swanson et al.

Frequently, a focal arrhythmia substrate resides at the base, or within, one or more pulmonary veins, wherein the atrial tissue extends. The automaticity created by these substrates results in ectopic atrial tachycardia. Although the effect caused by the depolarization wavefront propagating from the pulmonary vein containing the substrate resembles that caused by re-entrant pathways within the atria, the atrial fibrillation is actually caused by a single focal arrhythmia substrate within the pulmonary vein. Arrhythmia substrates residing at the base of, or within, a pulmonary vein may alternatively participate in circuit with the depolarization wavefront propagating around a single vein or within a slow conduction zone residing near or within the vein.

Current techniques of eradicating these substrates include steering a conventional ablation catheter within the target pulmonary vein and mapping this region to pinpoint the substrate. However, this is a time consuming and difficult process. Either extensive mapping must be performed within the pulmonary vein to accurately locate the target ablation site, or multiple lesions must be created to, in effect, "carpet bomb" the substrate. Moreover, the substrate may be located deep within the pulmonary vein, thereby making the manipulations required to steer the catheter's distal tip to the target site difficult.

Another technique involves creating circumferential lesions in endocardial and surrounding tissues, e.g., in and around pulmonary veins, in the inferior vena cava, the superior vena cava, and the sinus coronary, to thereby isolate focal arrhythmia substrates. A variety of catheters with electrodes mounted on their distal ends may be used in performing this technique, an especially popular type being balloon catheters. When balloon catheters are used, at least a portion of the surface area of the balloon typically comprises an electrode that performs the ablation.

There are drawbacks to using conventional balloon catheters for creating circumferential lesions in endocardial and surrounding tissues. A serious drawback is that due to their typically large profiles, known balloon catheters tend to completely block blood flow in the vein or artery where the balloon is inflated. Furthermore, these balloon catheters may not work with 150 watt/2.0 amp maximum radio frequency (RF) generators because of the increased surface area created by the inflated balloon. Yet another drawback is that different sized balloon catheters are required for the different sizes of veins and arteries.

Accordingly, there is a need for a balloon catheter that can electrically isolate veins by creating circumferential lesions in tissue, such as in endocardial and surrounding tissue, without substantially obstructing the flow of blood, and that can be used over a wide range of different sized veins and arteries. Furthermore, there is a need for a balloon catheter that can be used with 150 watt/2 amp generators.

SUMMARY OF THE INVENTION

The present invention addresses the aforementioned problems and is directed to methods and apparatus for creating circumferential lesions in and around veins, coronary vessels, and other parts of the body, without substantially obstructing blood flow. In particular, the present invention is designed to ablate tissue within a fluid carrying vessel, such as a blood vessel, while at the same time providing open channels for the fluid to flow around the apparatus.

In a first aspect of the present inventions, an ablation catheter is provided. The ablation catheter includes an elongate catheter body and an electrode structure mounted on a distal end of the catheter body, wherein the electrode structure includes a plurality of radially disposed inflatable chambers, e.g., four chamber.

In the preferred embodiment, each of the inflatable chambers has an exterior wall that peripherally surrounds an interior region. By way of non-limiting example, the exterior wall can be common to the plurality of inflatable chambers, in which case, adjacent inflatable chambers will be separated by a rib. Or each inflatable chamber comprises a distinct wall, in which case, the exterior wall will be formed by an aggregate of the plurality of distinct walls. The electrode structure is capable of delivering RF ablation energy. Alternatively, the electrode structure can be capable of delivering other types of ablative energy, such as microwave, ultrasonic, cryoablation, resistive heating, etc. In the preferred embodiment, ablation energy is delivered by the exterior wall of the electrode structure. By way of non-limiting example, the exterior wall can be formed of a microporous material or a conductive material.

In the preferred embodiment, the elongate catheter body is composed of an inner shaft having an inner shaft lumen, a stiffening mandrel disposed within the inner shaft lumen, and an outer shaft having an outer shaft lumen, wherein the inner shaft is disposed within the outer shaft lumen. The outer shaft includes a plurality of inflation lumens in communication with the interior regions of the inflatable chambers, which deliver an inflation medium to the inflatable chambers, and the inner shaft includes a plurality of lumens that house electrical leads for delivering ablation energy to the electrode structure. The ablation catheter may have a handle mounted on the proximal end of the catheter body and a radiopaque marker disposed on the distal end of the catheter body, thereby allowing the physician to properly orient the ablation catheter within the patient's body.

Other and further objects, features, aspects, and advantages of the present inventions will become better understood with the following detailed description of the accompanying drawings.

BRIEF DESCRIPTION OF THE DRAWINGS

FIG. 15A is an illustration of a preferred embodiment of a stepped balloon electrode structure used in the catheter assembly, wherein all of chambers are in a deflated configuration;

FIG. 15B is an illustration of the stepped balloon electrode structure of FIG. 15A, wherein one of the chambers is in an inflated configuration;

DETAILED DESCRIPTION OF THE PREFERRED EMBODIMENTS

Figure 1:
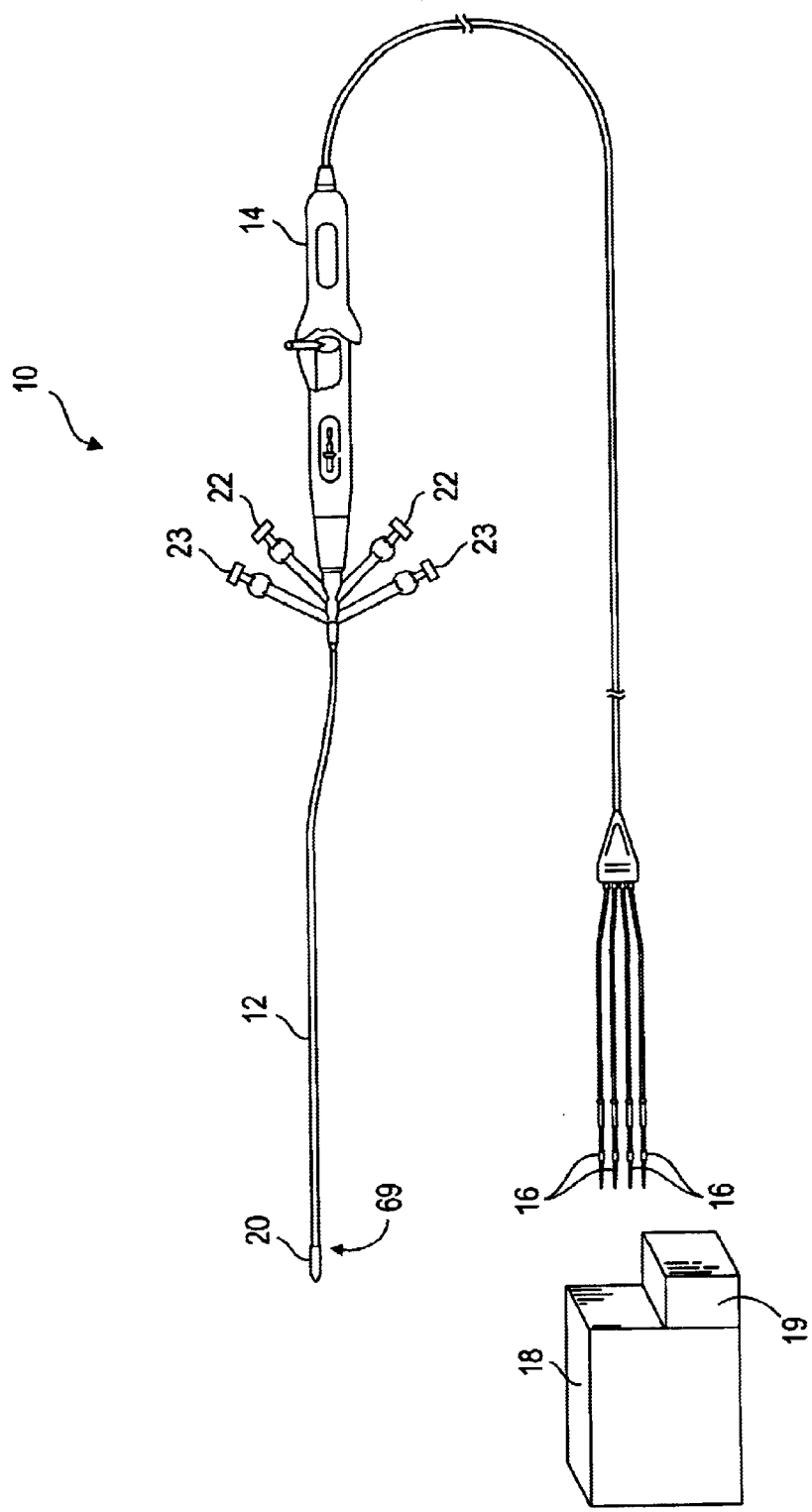
FIG. 1 is an illustration of a preferred embodiment of a catheter system constructed in accordance with the present inventions.

Referring to FIG. 1, a presently preferred embodiment of an ablation catheter assembly 10 includes a flexible catheter tube 12 made of a polymeric, electrically nonconductive material, like polyethylene, polyurethane, or PEBAX® (i.e., polyether block amide). The catheter tube 12 has an open proximal end that is connected to a handle 14, and a distal end that is connected to a balloon electrode structure 20 for use within blood vessels, such as a pulmonary vein, to perform ablation techniques in order to form lesions within the blood vessels without substantially obstructing blood flow.

Figure 2:
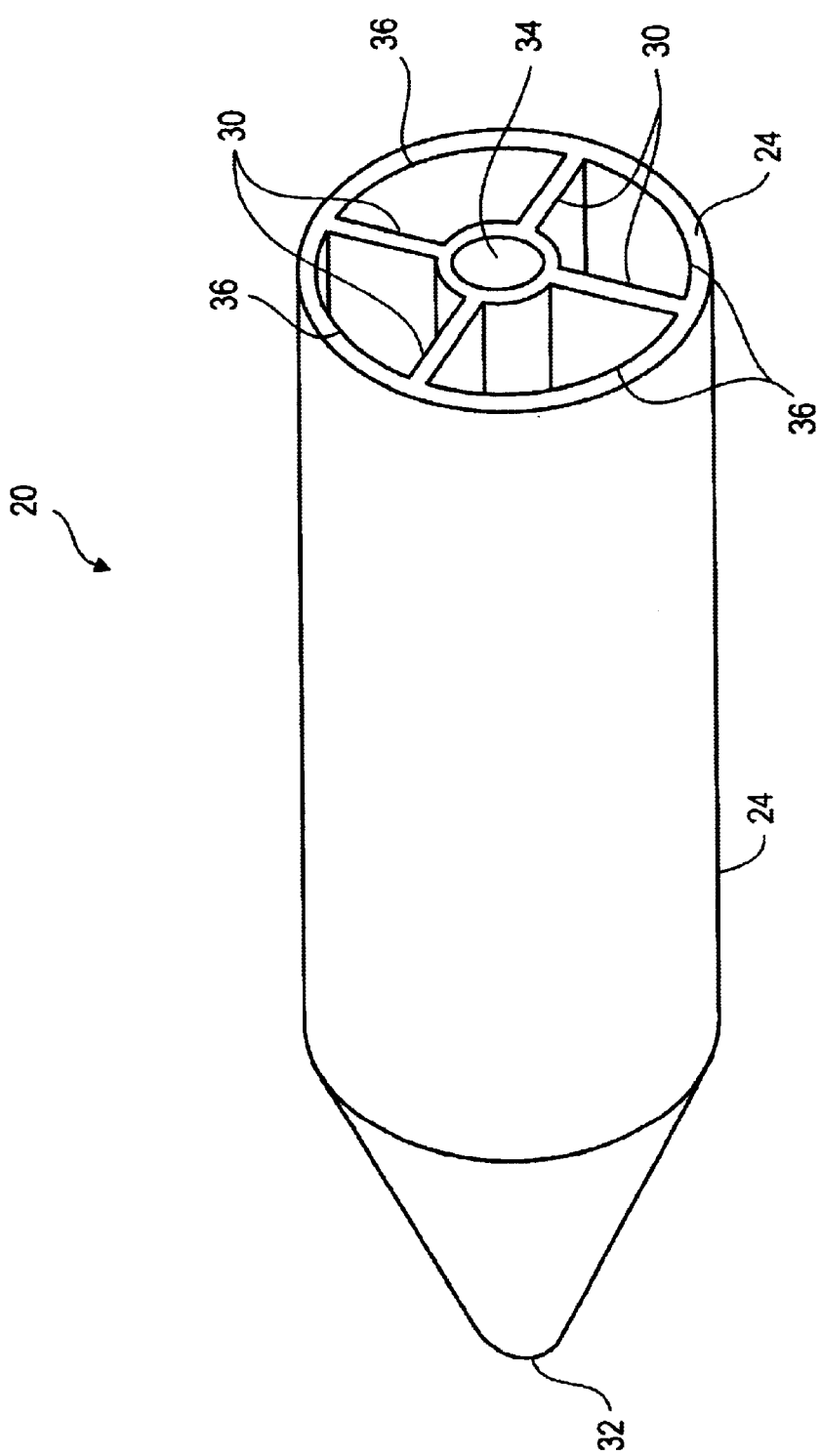
FIG. 2 is a perspective illustration of a preferred embodiment of a balloon electrode structure used in the catheter system.

Referring now to FIG. 2, the balloon electrode structure 20 includes a single structure with a plurality of inflatable chambers 36, a plurality of ribs 30, and an exterior wall 24. The balloon electrode structure 20 is mounted onto an inner shaft 50 (shown in FIG. 6A), wherein the lumen 34 is adapted to receive such inner shaft 50.

The balloon electrode structure 20 is preferably manufactured using a casting process, wherein the structure 20 is molded out of a suitable elastomeric, bio-compatible polymer, such as hydrophillic silicone. Other suitable polymers include Santoprene, polyurethane, C-flex, Kraton, latex, and neoprene, as well as other porous polymers that are known in the art and would be suitable for use in the present invention. In the illustrated embodiment, at least portions of exterior wall 24 located atop each inflatable chamber 36 include pores (not shown) that are sized to block the passage of macromolecules, while allowing the passage of ions.

The geometry of the balloon electrode structure 20 can be altered between a collapsed, low profile geometry, in which case, all of the inflatable chambers 36 are deflated, and an expanded, high profile geometry, in which case, one or more of the inflatable chambers 36 are inflated. When in the low profile geometry, the balloon electrode structure 20 is easily tracked through a small diameter sheath, such as a 9.5 F sheath. When in the high profile geometry, the balloon electrode structure 20 can accommodate a wide range of blood vessel diameters by virtue of the inflatable chambers 36.

As shown in FIG. 2, a presently preferred embodiment utilizes four inflatable chambers 36 radially situated within the balloon electrode structure 20. In alternative embodiments, greater than or less than four inflatable chambers 36 may be used. The inflatable chambers 36 share the exterior wall 24 of the balloon electrode structure 20, and are separated by the internal ribs 30. A tip 32 of the balloon electrode structure 20 is preferably rounded to form a smooth tip to prevent injury to the body while in use.

Figure 3:
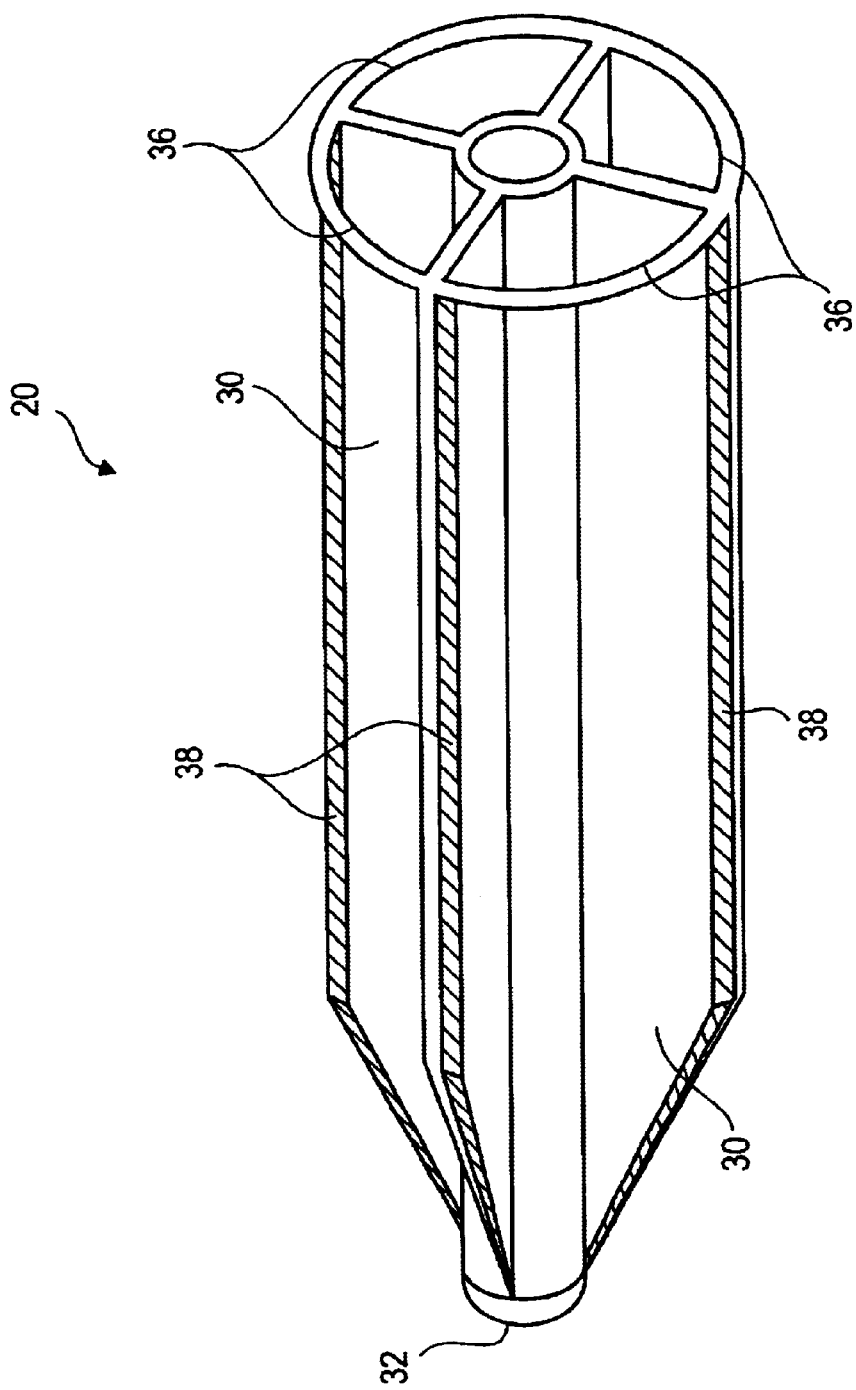
FIG. 3 is an cut-away illustration of the internal configuration of the balloon electrode structure.

Referring now to FIG. 3, the internal configuration of the preferred balloon electrode structure 20 is shown. The exterior wall 24 of the balloon electrode structure 20 is not shown for purposes of clarity, but points of attachment 38 between the exterior wall 24 and the ribs 30 are shown for reference. As seen in FIG. 3, the inner structure of the balloon includes the plurality of ribs 30, which separate the individual chambers 36 from one another. The ribs 30 run the entire length of the balloon electrode structure 20, and taper down to the tip 32 of the balloon electrode structure 20, as shown in FIG. 3.

Figure 4A:
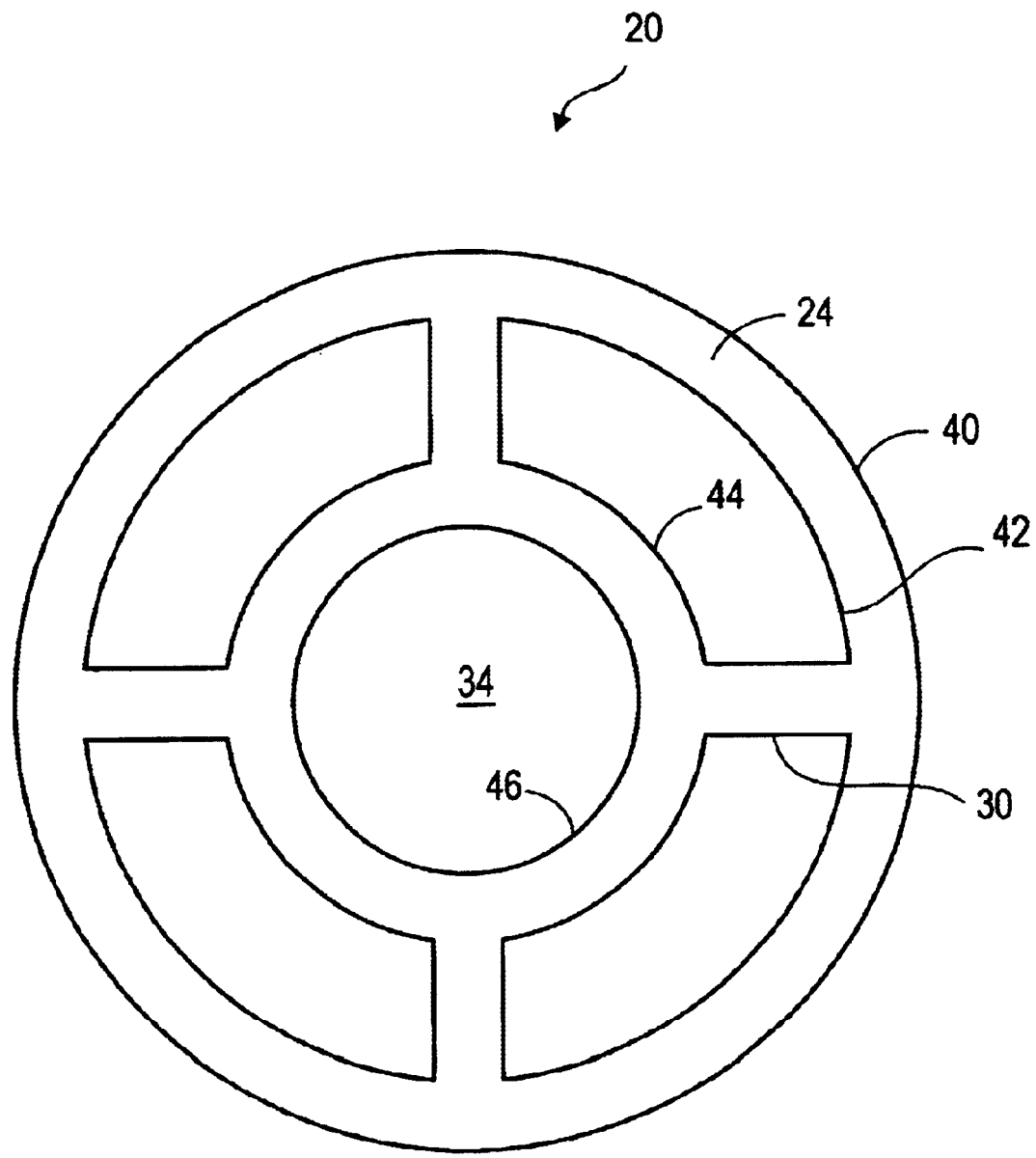
FIG. 4A is a cross-section diagram of the balloon electrode structure.

Turning now to FIG. 4A, a cross-sectional diagram of the preferred balloon electrode structure 20 is shown. By way of non-limiting example, an outer surface 40 of the exterior wall 24 has a diameter between 0.080 and 0.150 inches, preferably around 0.115 inches, and an inner surface 42 of the exterior wall 24 has a diameter between 0.052 and 0.160 inches, preferably around 0.105 inches. The lumen 34 has an outer surface 44 with a diameter between 0.025 and 0.075 inches, preferably around 0.050 inches, and an inner surface 46 with a diameter between 0.020 and 0.060 inches preferably around 0.040 inches. The inner surface 46 diameter will really depend on the diameter of the inner shaft 50 (shown in FIG. 6A) since lumen 34 will receive the inner shaft 50 when the balloon electrode structure 20 is mounted on the inner shaft 50. Finally, the width of each of the ribs 30 is between 0.005 and 0.015 inches, preferably around 0.010 inches.

Figure 4B:
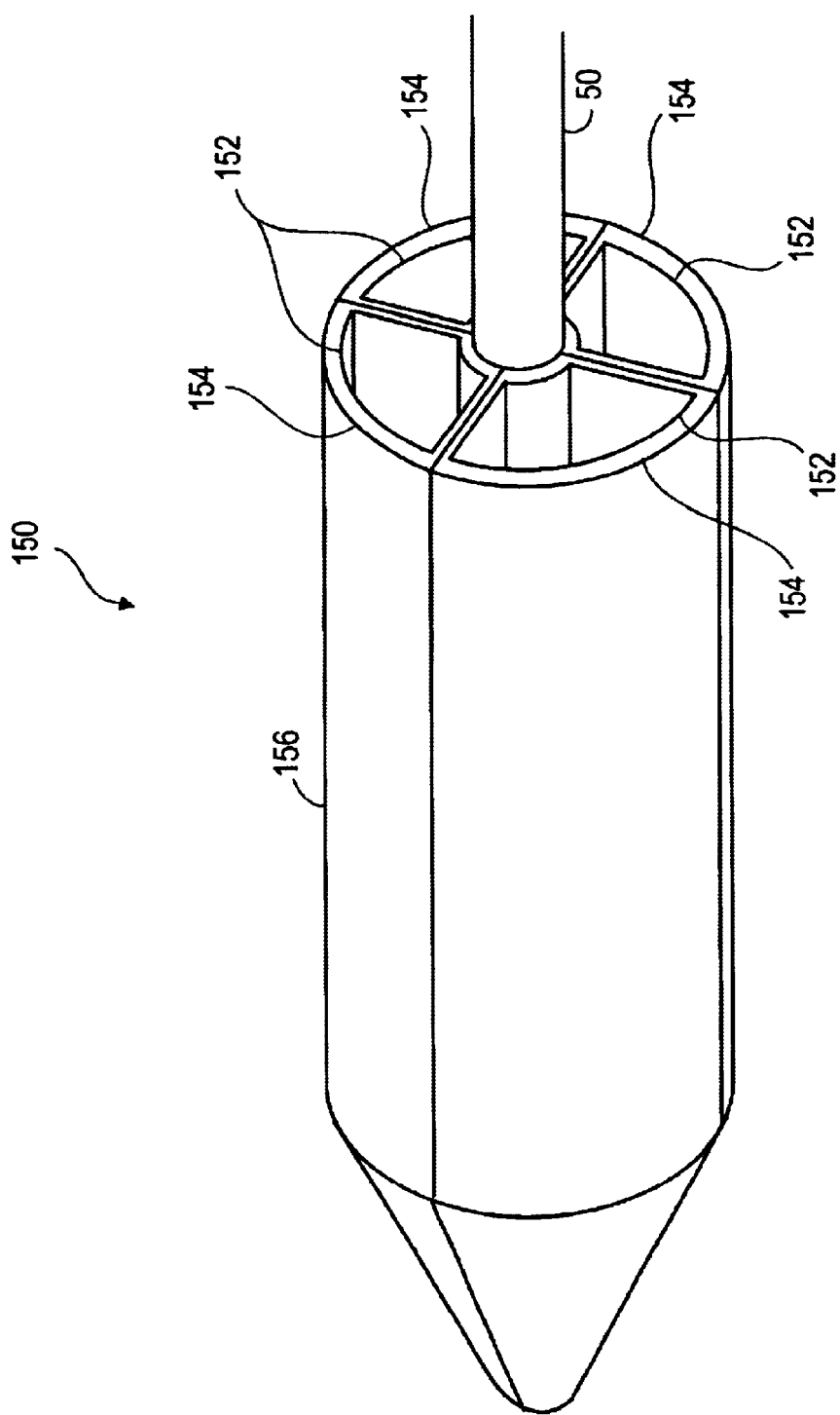
FIG. 4B is an illustration of an alternative preferred embodiment of a balloon electrode structure used in the catheter assembly.

In FIG. 4B, an alternative embodiment of a balloon electrode structure 150 is illustrated. Unlike balloon electrode structure 20, which includes inflatable chambers 36 that share a common exterior wall 24, the balloon electrode structure 150 includes inflatable chambers 152 that are formed from separate and divisible balloons 154. Thus, the balloon electrode structure 150 includes an exterior wall 156 that is formed from an aggregate of the exterior balloon walls of the individual balloons 154. The balloons 154 are radially mounted onto the inner shaft 50, and are constructed so as to form a complete cylindrical structure when all of the balloons 154 are inflated.

Figure 5:
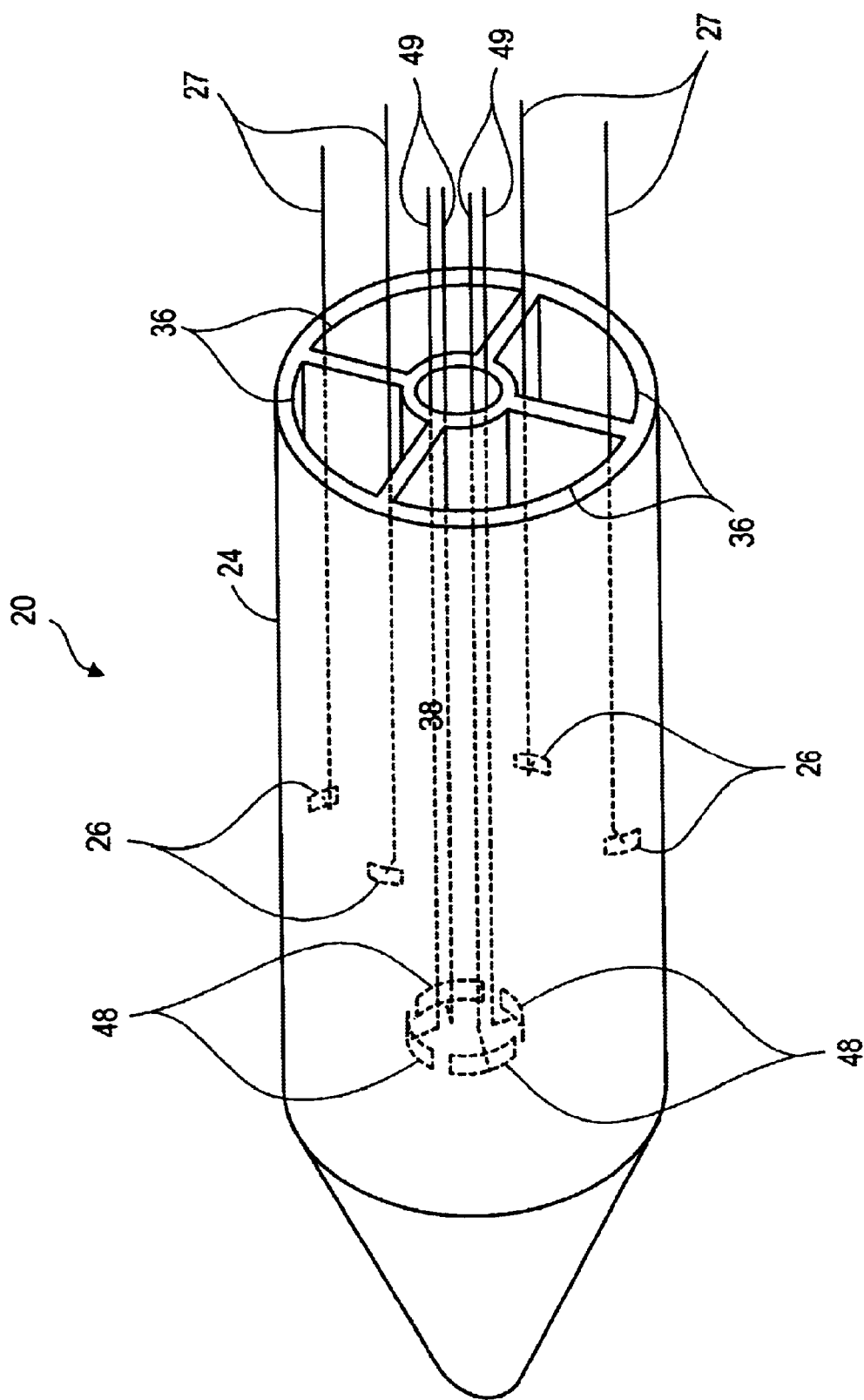
FIG. 5 is a perspective illustration of the balloon electrode structure with the electrodes and RF leads visible (in phantom)

Turning to FIG. 5, the balloon electrode structure 20 includes a plurality of interior electrodes 48, which are respectively coupled to radio frequency (RF) leads 49. As will be described below, the RF leads 49 are routed back through the catheter tube 12. Each of the interior electrodes 48 is mounted within an inflatable chamber 36. The interior electrodes 48 may include, by way of non-limiting example, a coil formed from a suitable material. Such suitable materials preferably have both a relatively high electrical conductivity and a relatively high thermal conductivity. Materials possessing these characteristics include, among others, gold, platinum, platinum/iridium, conductive ink epoxy, or a combination thereof. In particular, noble metals are preferred.

As will be described in further detail below, when the inflatable chambers 36 are filled with an ionic solution, and the interior electrodes 36 are energized, electrical energy is ionically transported from the energized ionic solution, through the pores in the wall 24, and into the tissue being ablated. Preferred embodiments of microporous balloon structures and corresponding methods of manufacture are described in U.S. Pat. No. 5,961,513, issued to Swanson et al., which is fully and expressly incorporated herein by reference.

In an alternative embodiment, the balloon electrode structure 20 itself may be non-porous and conductive, in which case, one or more electrodes can be disposed on the outside surface of the balloon electrode structure 20, or the balloon electrode structure 20 itself can be constructed from a conductive material. In such an embodiment, the ablation energy is transmitted to the tissue from the outer conducting surface of the balloon electrode structure 20, rather than by the ionic transport of energy through the wall 24 of the balloon electrode structure 20. Preferred embodiments of electrically conductive balloon structures and corresponding methods of manufacture are described in U.S. Pat. No. 5,891,136 issued to McGee et al., which is fully and expressly incorporated herein by reference.

As shown in FIG. 5, the balloon electrode structure 20 also includes temperature sensing elements 26 to monitor the temperature. By way of non-limiting example, the temperature sensing elements 26 can take the form of thermistors or thermocouples. The connection of the temperature sensing elements 26 to the balloon electrode structure 20 can be achieved in various ways, such as by attachment to the interior surface of the balloon electrode structure 20, or attachment to the exterior surface of the balloon electrode structure 20. Preferably, however, the temperature sensing elements 26 are mounted on the inside surface of the balloon within one or more of the inflatable chambers 36 at a location that represents the hottest region during an ablation procedure (this is not necessarily shown in FIG. 5). The temperature sensing elements 26 are connected to temperature sensing wires 27, which, as will be described below, are routed back through the catheter tube 12. The temperature sensor wires 27 are preferably shielded to block RF interference emitted by the RF leads 49.

Figure 6A:
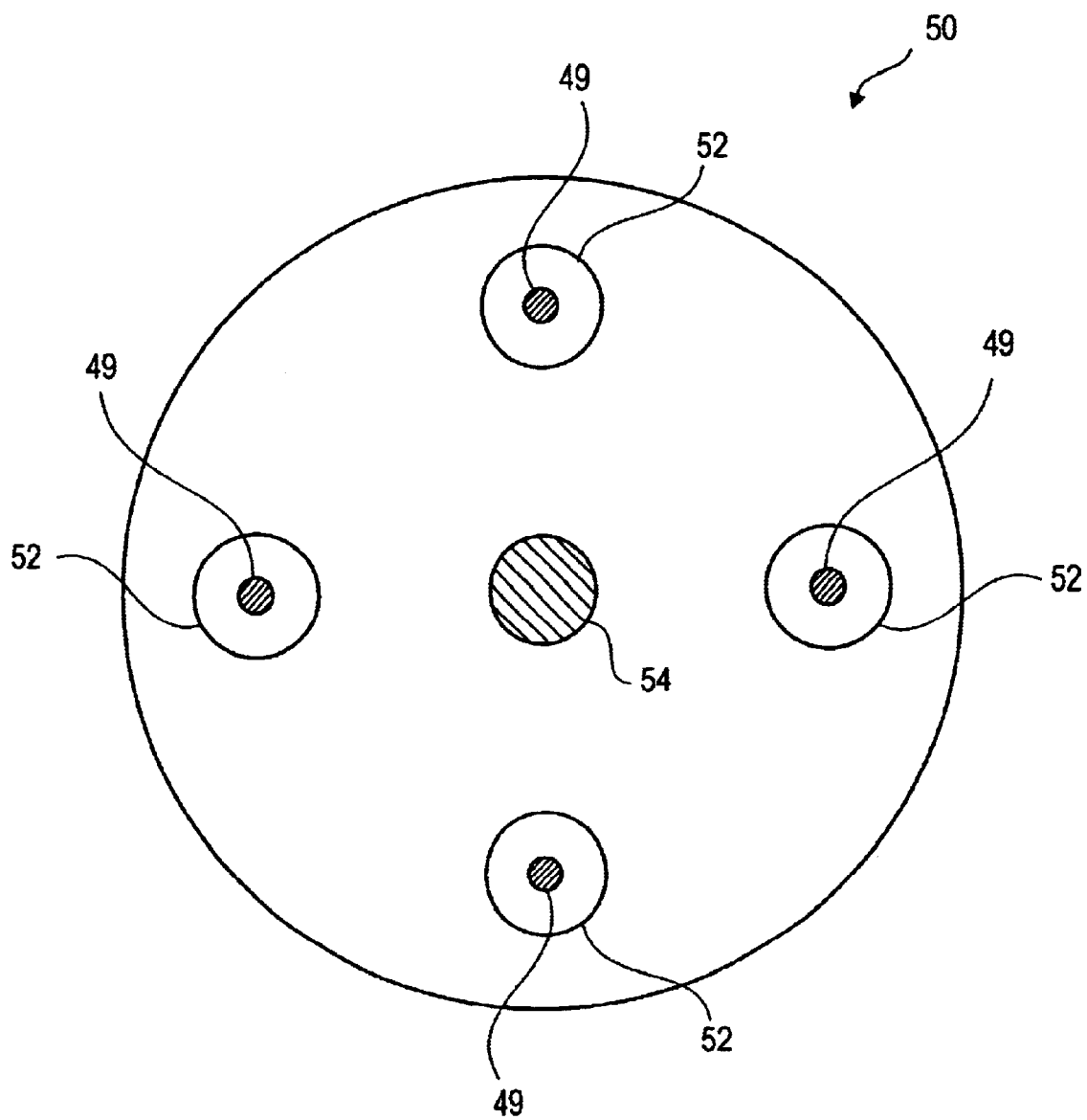
FIG. 6A is a cross-section diagram of a preferred embodiment of an inner shaft of a catheter tube used in the catheter assembly.
Figure 6B:
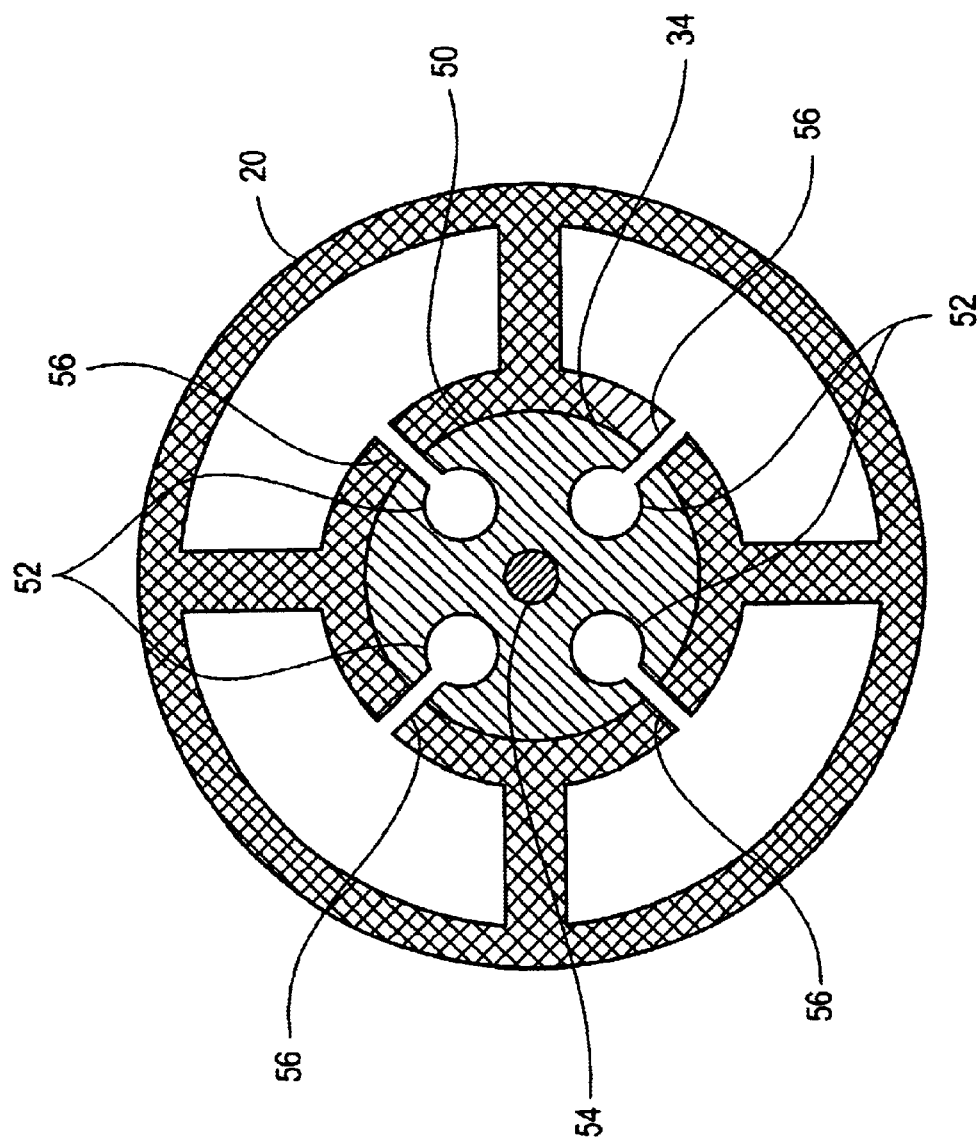
FIG. 6B is a cross-section diagram of the inner shaft of the catheter tube disposed within the balloon electrode structure.

Turning now to FIGS. 6A, 6B, and 7, the catheter tube 12 includes the inner shaft 50, which was briefly discussed above, and an outer shaft 60. Both the inner shaft 50 and outer shaft 60 include long flexible tubes of a type commonly used in the art, constructed from a suitable material, such as Pebax. Other suitable materials include nylon, polyethylene, polyurethane, polyvinylidene fluoride, or other flexible polymers known in the art to be suitable for use in the present invention.

The inner shaft 50 carries the balloon electrode structure 20, and specifically, is disposed within the lumen 34 of the balloon electrode structure 20. The inner shaft 50 also provides a means for conveying the ablation wires 49 to the balloon electrode structure 20. The outer shaft 60 houses the inner shaft 50 and provides a means for conveying liquid medium, as well as temperature sensing wires to the balloon electrode structure 20. In an alternative embodiment, the inner shaft 50 and the outer shaft 60 may be combined into a single, multi-lumen tube.

As illustrated in the cross-sectional diagram of FIG. 6A, the inner shaft 50 includes a plurality of lumens 52 through which the RF leads 49 are threaded from the interior electrodes 48 of the balloon electrode structure 20. In the illustrated embodiment, there are four lumens 52, one for each inflatable chamber 36. FIG. 6B illustrates a cross-sectional diagram of the inner shaft 50 inside the balloon electrode structure 20 at a point where the two structures are in communication with one another. A plurality of passages 56 are provided to allow the RF leads 49 to pass from the inner shaft 50 to interior electrodes 48 located within the chambers 36 of the balloon electrode structure 20. Preferably, there are fluid tight seals (not shown) located at the passages 56 to prevent fluid from passing into the inner shaft 50 from the inflatable chambers 36. By way of non-limiting example, the inner shaft 50 may have a diameter between 0.020 and 0.060 inches, preferably around 0.040, and the lumens 52 may be between 0.005 and 0.015 inches, preferably around 0.010 inches in diameter.

The inner shaft 50 also includes a lumen for placing a stiffening mandrel 54, which is located along a center axis of the inner shaft 50. The stiffening mandrel 54 is used to provide support and a degree of rigidity for the inner shaft 50 to improve the steerability of the catheter assembly 10, and to provide axial support to the balloon electrode structure 20 during manipulation of the catheter assembly 10. Manipulation of the balloon electrode structure 20 through the vasculature and heart can be accomplished by use of a steering mechanism incorporated into the handle 14 of the catheter, using techniques that are generally known in the art. The details of such steering mechanisms are disclosed in U.S. Pat. No. 5,254,088, issued to Lundquist et al., which is fully and expressly incorporated herein by reference.

The inner shaft 50 further includes a radio-opaque marker (not shown), which is placed on the outer surface thereof at the mid-region of the balloon electrode structure 20. In an alternate embodiment, two or more radio-opaque markers may be placed on the outer surface of the inner shaft 50 at both ends of the balloon electrode structure 20. These opaque markers are preferably used for orientation purposes, so that the physician can guide the balloon electrode structure 20 under fluoroscopy to the targeted site. The temperature sensing elements 26 can be on the same side as the radio-opaque marker, or on the opposite side, as long as the physician is aware of the relative position of them. Further details regarding the structure and use of temperature sensing elements and radio-opaque markers are disclosed in U.S. Pat. No. 5,582,609, issued to Swanson et al., which is fully and expressly incorporated herein by reference.

Figure 7A:
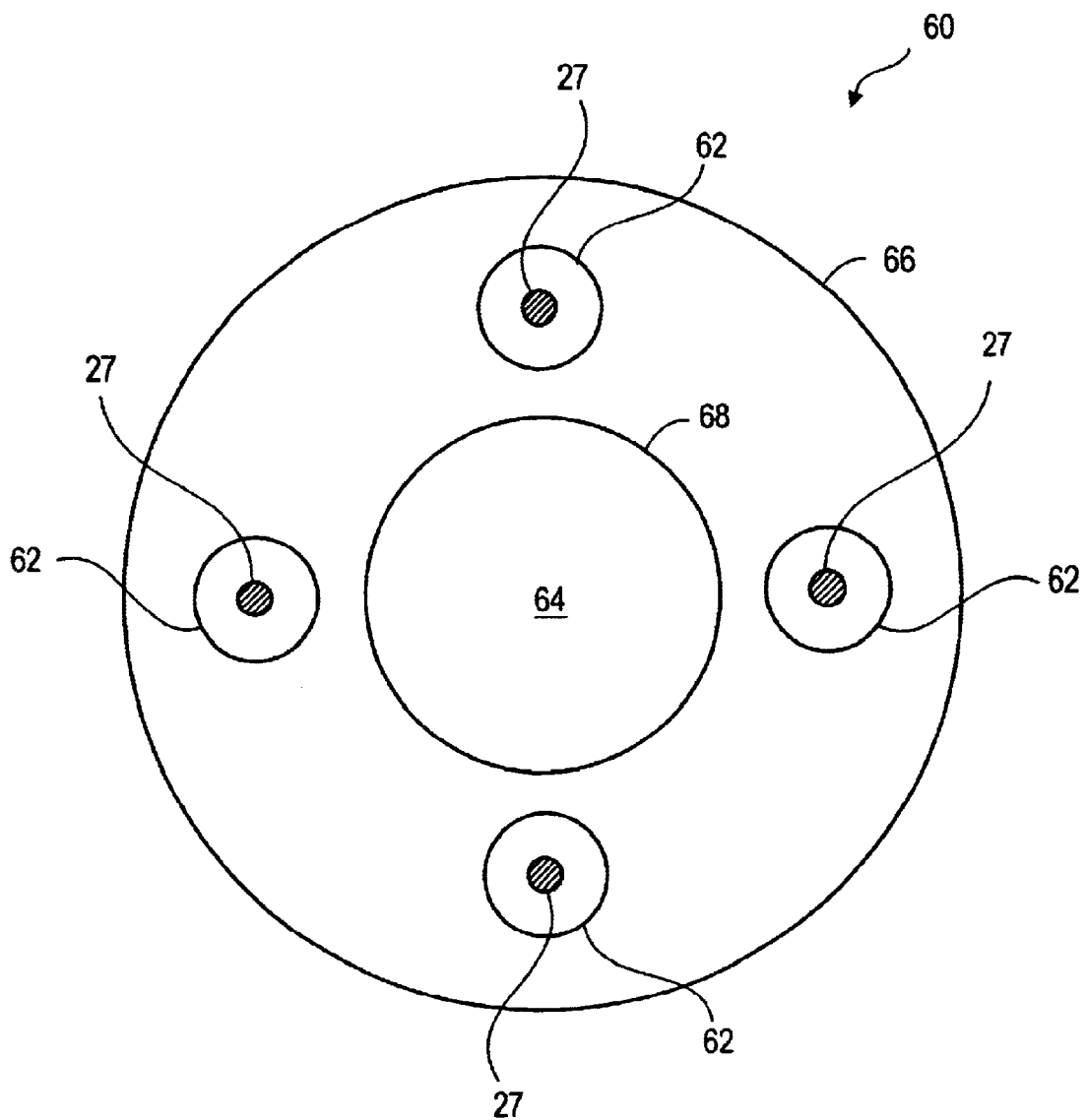
FIG. 7A is a cross-section diagram of a preferred embodiment of an outer shaft of a catheter tube used in the catheter assembly.

As illustrated in the cross-sectional diagram of FIG. 7A, the outer shaft 60 includes a lumen 64 to receive the inner shaft 50, and a plurality of inflation/deflation lumens 62, one for each inflatable chamber 36 of the balloon structure 20.

The inflation/deflation lumens 62 are in fluid communication with the respective inflatable chambers 36, and are not only used to convey inflation medium to and from the inflatable chambers 36, but are also used to house and route the temperature sensing element wires 27 to the temperature sensing elements 26. In an alternate embodiment, separate lumens may be used to carry the temperature sensing element wires 27.

Figure 7B:
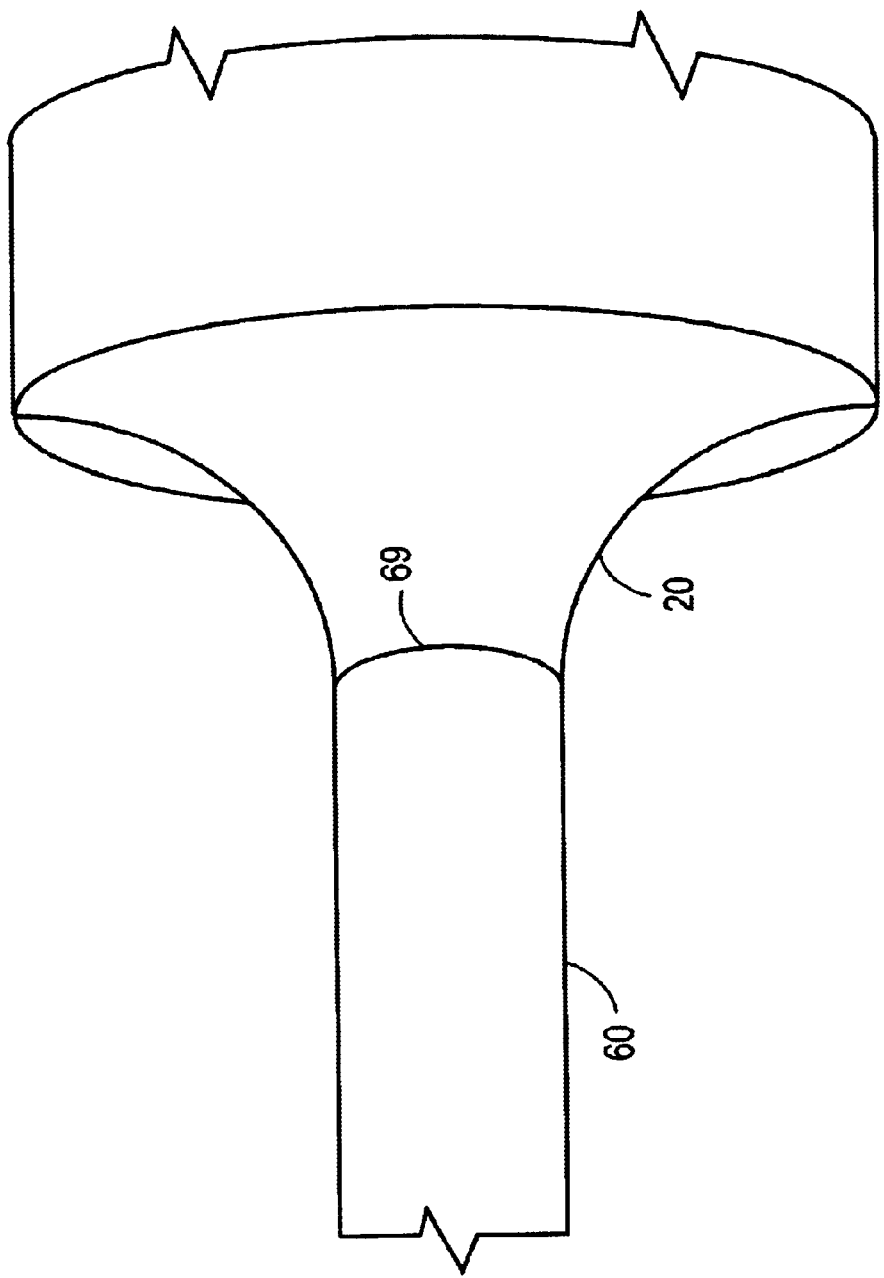
FIG. 7B is an illustration of the outer shaft of the catheter tube mounted to the balloon electrode structure.

As shown in FIG. 7B, the outer shaft 60 is coupled to the balloon electrode structure 20 at an interface 69 near the distal end of the catheter 10. The outer shaft 60 is preferably butt bonded to the balloon electrode structure 20 using an adhesive such as cyanoacrylates, UV adhesives, RTV type of adhesives, or epoxies. For added mechanical integrity, the outer shaft 60 may be bonded to the balloon electrode structure 20 at the interface 69 by inserting thin tubes (not shown) in the lumens 62 of the outer shaft 60 and bonding them using adhesives as described above. Alternately, the outer shaft 60 may be bonded to the balloon electrode structure 20 by using a larger, thin-walled, single lumen tube as a sleeve (not shown) over the interface 69. This sleeve can be bonded in place using the same adhesives outlined above.

Furthermore, there is a fluid tight seal between each inflation/deflation lumen 62 and its respective inflatable chamber 36 to prevent any fluid leak from the chamber. As illustrated, the proximal end of the balloon electrode structure 20 is constrained by the outer shaft 60, and thus, does not inflate when the balloon electrode structure 20 is generally inflated.

By way of non-limiting example, the diameter of the outer surface 66 of the outer shaft 60 may be between 0.080 and 0.150 inches, preferably around 0.105 inches, and the diameter of the lumen 64 may be between 0.020 and 0.060 inches, preferably around 0.040 inches. At a minimum, lumen 64 must be large enough to accommodate the inner shaft 50 and allow it to easily slide back and forth within the lumen 64. The reason for this is that during construction of the inner and outer shafts, it is difficult to extrude both the inner shaft 50 and the outer shaft 60 as one piece. Thus, the inner shaft 50 and outer shaft 60 must be fabricated separately, and then joined by inserting the inner shaft 50 into the outer shaft 60. Once joined, the shafts are substantially locked in place and no longer move with respect to one another.

The diameter of each of the inflation/deflation lumens 62 may be between 0.010 and 0.030 inches, preferably around 0.020 inches. The inflation/deflation lumens 62 are located equidistant from one another and, by way of non-limiting example, may be between 0.001 and 0.01 inches, preferably 0.005 inches, from the outer surface 66 of the outer shaft 60, and between 0.001 and 0.01 inches, preferably 0.005 inches, from a perimeter 68 of the lumen 64.

Referring back to FIG. 1, the handle 14 is formed at the proximal end of the catheter tube 12. The handle 14 is preferably coupled to the catheter shaft 12 via a strain relief (not shown), which is known in the art. The handle 14 includes respective inflation and deflation ports 22 and 23, which are in fluid communication with the inflation/deflation lumens 62, so that a user can alternately inflate or deflate the inflatable chambers 36 of the balloon electrode structure 20 from the handle 14. The handle 14 also includes connectors 16 in which the RF wires 49 and temperature sensing wires 27 terminate. The connectors 16, in turn, are connected to an RF generator 18 and associated controller 19. Thus, the interior electrodes 48 and temperature sensing elements 26 are electrically coupled to the respective RF generator 18 and controller 19, allowing RF power to be delivered to the inflatable chambers 36, and thus, the targeted tissue, under temperature-feedback control.

Various types of RF generators 18 may be used with the catheter assembly 10, including a 150 watt/2 amp RF generator. The controller 19 is associated with the RF generator 18, either as an integrated unit or as a separate box, and governs the delivery of RF ablation energy to the balloon electrode structure 20 according to pre-established criteria. This also allows the catheter assembly 10 to be operated in power control mode. Tissue temperatures sensed by the temperature sensing elements 26 are processed by the controller 19. Based upon temperature input, the controller 19 may adjust the time and power level of RF energy transmissions by the RF generator 18, in order to achieve desired lesion patterns and other ablation objectives.

Operation of the catheter assembly 10 in creating a lesion within a vessel targeted for ablation is now described. In the preferred method, the RF energy from the RF generator 18 is preferably transmitted to the tissue being ablated via ionic transport. In this technique, a liquid inflation medium, such as water, saline solution, or other bio-compatible fluid containing ions, is conveyed under positive pressure through the inflation port 22 in the handle 14 and into the inflation/deflation lumen 62. The liquid medium fills the interior of the inflatable chambers 36 and exerts pressure on the inside of the chambers 36 to urge them from their collapsed geometry to their inflated geometry. Constant exertion of pressure through the inflation/deflation lumen 62 maintains the chambers 36 in their inflated geometry. Preferably, the chambers 36 are inflated to a degree that allows them to contact the vessel that the balloon electrode structure 20 is disposed within.

Figure 8:
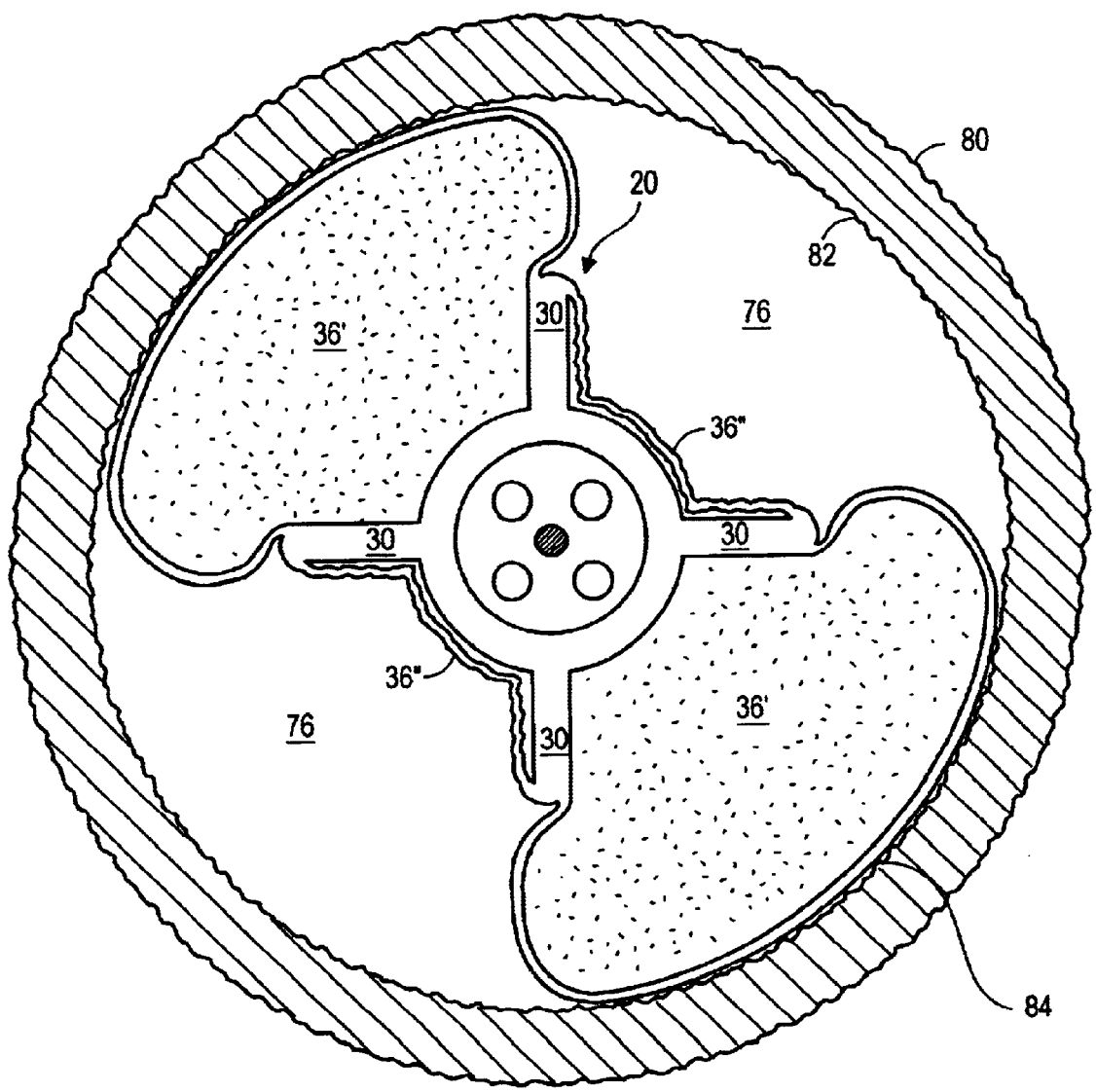
FIG. 8 is an illustration of the balloon electrode structure disposed within a blood vessel, wherein two opposing chambers of the balloon electrode structure are in an inflated configuration, and two opposing chambers of the balloon electrode structure are in a deflated configuration.

As illustrated in FIG. 8, two of the chambers 36' are inflated, and the other two chambers 36" are deflated. The inflated chambers 36' come into contact with an inner wall segment 84 of the blood vessel 80, while the deflated chambers 36", which are shown collapsed onto the ribs 30, furnish a channel 76 between the deflated chambers 36" and an inner wall segment 82 of the blood vessel 80. This channel 76 allows blood to flow freely past the balloon electrode structure 20, even while the catheter assembly 10 is performing an ablation procedure.

It is preferred that less than all of the chambers 36, more preferably about half of them, be inflated at a time, thereby allowing blood to flow through channels 76 created by the deflated chambers 36". It is also preferred that any inflated chambers 36' be located on opposing sides of the balloon electrode structure 20, thus helping to anchor the balloon electrode structure 20 in place as the ablation procedure is performed. For example, in the presently preferred embodiment where four inflatable chambers 36 are implemented, two of the chambers 36' located in opposing quadrants would be inflated simultaneously.

The composition of the electrically conductive liquid medium used for inflating the chambers 36 may vary. Preferably, the selected liquid medium possesses a low resistivity to decrease ohmic losses, and thus ohmic heating effects, within the balloon electrode structure 20. By way of one preferred example, the liquid medium may include a hypertonic saline solution, having a sodium chloride concentration at or about saturation, which is about 10% weight by volume. Hypertonic 10% saline solution has a low resistivity of only about 5 ohm-cm, compared to blood resistivity of about 150 ohm-cm and myocardial tissue resistivity of about 500 ohm-cm. The electrical resistivity of the balloon electrode structure 20 can be controlled by specifying the pore size of the material, the porosity of the material, and the water absorption characteristics (hydrophilic versus hydrophobic) of the material.

Once the inflated balloon electrode structure 20 is in position, the RF generator 18 is operated to convey RF energy to the wall segment 84 of the vessel 80 to form a lesion thereon. Specifically, the RF generator 18 conveys RF energy to the internal electrodes 48. The liquid medium, in turn, establishes an electrically conductive path between the interior electrodes 48 and the wall segment 84 of the vessel 80. In other words, the ions convey RF ablation energy from the interior electrode 48, through the pores within the exterior wall 24, and to the wall segment 84 of the vessel 80.

The RF currents provided by the ions result in no net diffusion of ions, as would occur if a DC voltage were applied, although the ions do move slightly back and forth during the RF frequency application. Notably, this ionic movement (and current flow) in response to the applied RF energy does not require perfusion of the liquid medium through the pores of the exterior wall 24. In particular, due largely to mass concentration differentials across the pores, ions in the liquid medium will pass through—i.e., due to concentration differential-driven diffusion. Ion diffusion through the pores will continue so long as a concentration gradient is maintained across the exterior wall 24, wherein the ions provide the means for conducting current across the exterior wall 24. The ions convey RF energy through the pores and into wall segment 84 of the vessel 80 to a return electrode (not shown), which is typically an external patch electrode, thereby forming a unipolar arrangement.

In an alternate embodiment, when the balloon electrode structure 20 is conductive and non-porous, the interior electrodes 48 transmit the RF energy from the RF generator 18 directly to the exterior wall 24 itself, or to an electrode located on the exterior wall 24. The RF energy is then directly applied to the wall segment 84 of the vessel 80.

After the wall segment 84 of the vessel 80 is ablated, resulting lesions will extend over only portions of the vessel 80 adjacent the inflated chambers 36' since the areas of the inner wall segment 82 where the channels 76 were created for blood flow were not ablated. Because it is preferred that the lesions form a continuous ring, these remaining areas are then ablated by rotating the entire catheter and using the inflated chambers 36' to ablate any remaining tissue. Alternatively, the inflated chambers 36' may be deflated, and the deflated chambers 36" may be inflated, which allows the now inflated chambers 36" to perform the ablation procedure on the remaining tissue. In order to effectively maintain and lock the circumferential orientation of the balloon electrode structure 20 into position with respect to the anatomical structure being ablated, the user may presumably first inflate the deflated chambers 36", and then deflate the inflated chambers 36'.

Figure 9:
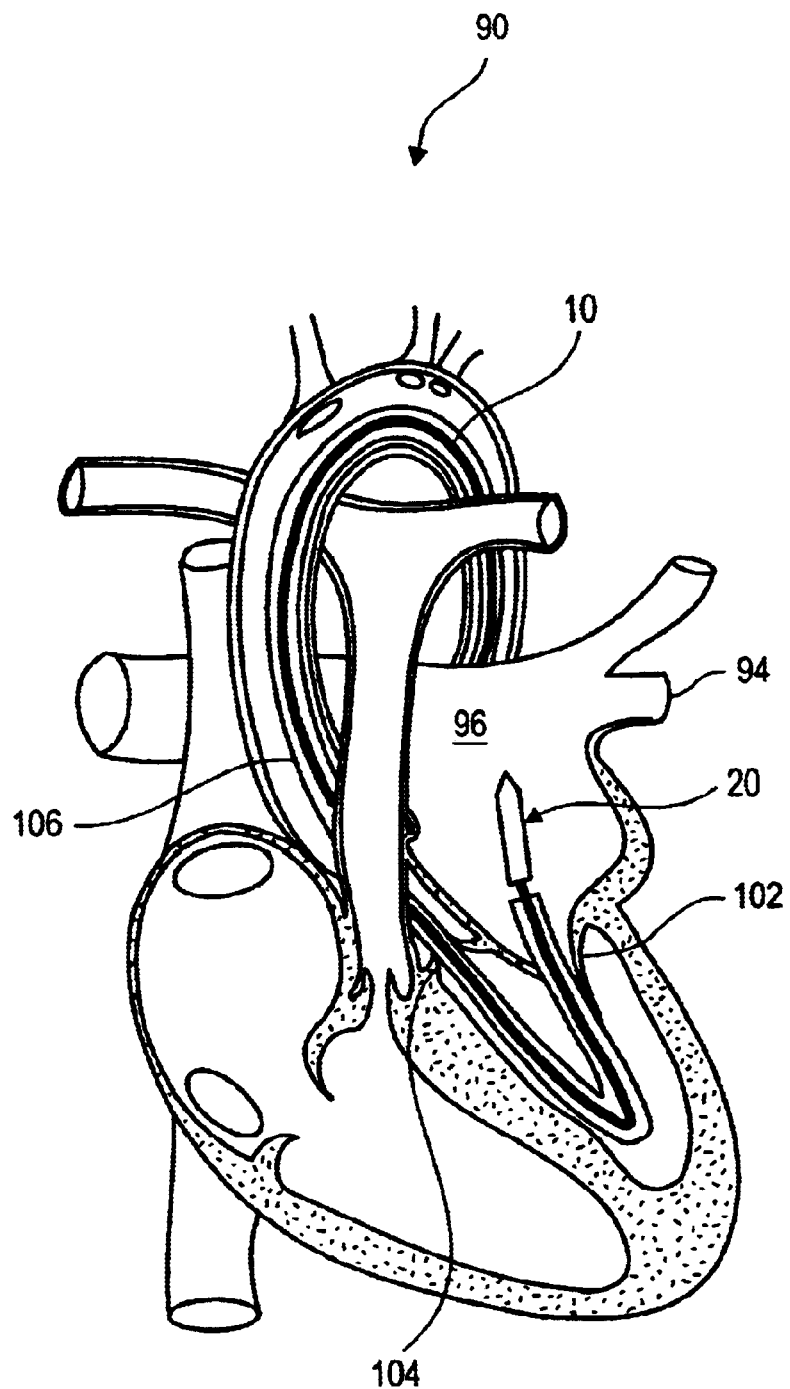
FIG. 9 is an illustration of one technique for guiding the balloon electrode structure into the left atrium of a heart.
Figure 10:
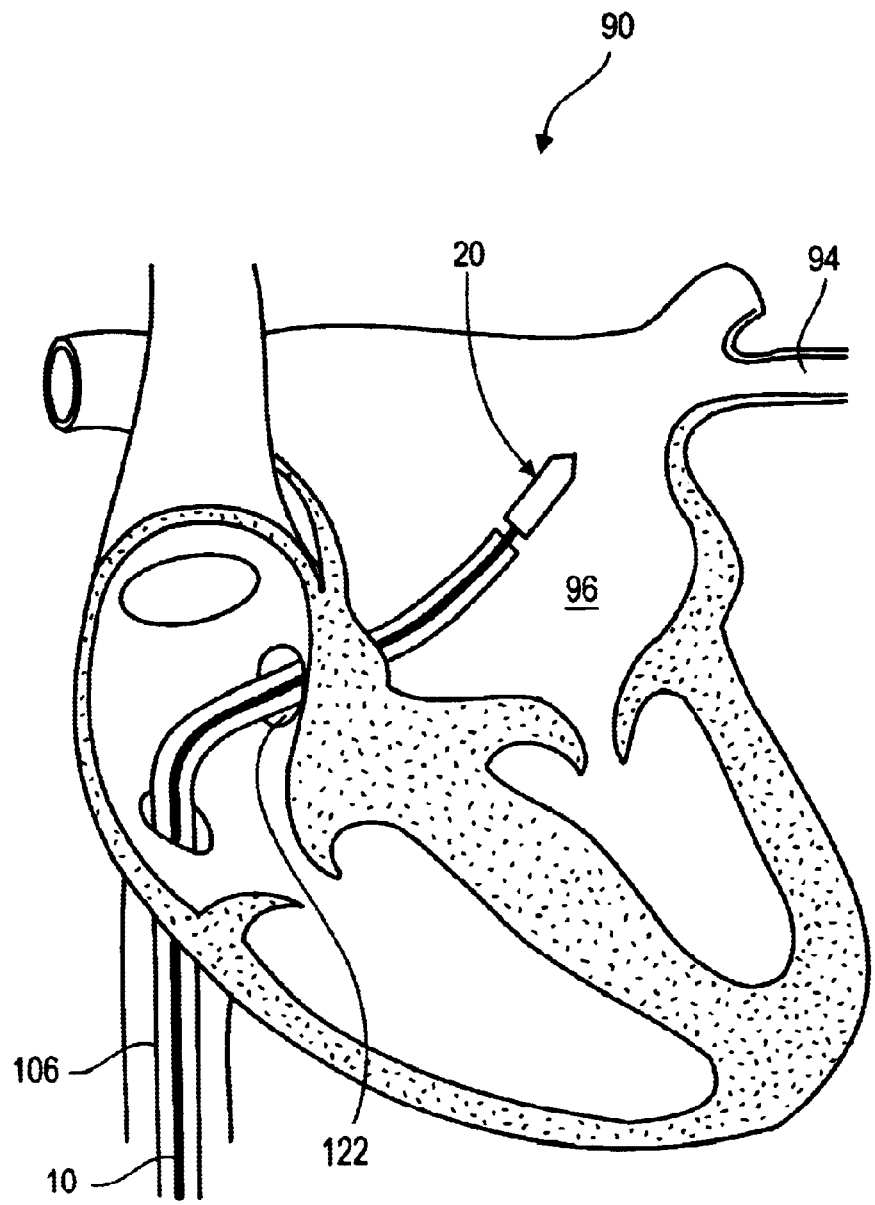
FIG. 10 is an illustration of a second technique for guiding balloon electrode structure into the left atrium of a heart.

Referring now to FIGS. 9–14, the catheter assembly 10 can be employed to isolate focal arrhythmia substrates in a pulmonary vein 94 by creating a circumferential lesion inside of the pulmonary vein 94. Referring specifically to FIG. 9, a conventional introducer guide sheath 106 (or a guide wire) is introduced into the left atrium 96 of the heart 90 using a conventional retrograde approach, i.e., through the respective aortic and mitral valves 104 and 102 of the heart 90. Alternatively, as shown in FIG. 10, the introducer guide sheath 106 can be introduced into the left atrium 96 using a transeptal approach, i.e., through the atrial septum 122. In either method, the catheter assembly 10 is introduced through the introducer guide sheath 106 until the balloon electrode structure 20 resides within the left atrium 96. A detailed description of methods for introducing a catheter into the left atrium via a transeptal approach is disclosed in U.S. Pat. No. 5,575,810, issued to Swanson et al., which is fully and expressly incorporated herein by reference. Once inside the left atrium 96, the physician can deliver the balloon electrode structure 20 into a desired pulmonary vein 94 by employing a steering mechanism on the handle 14.

Figure 11:
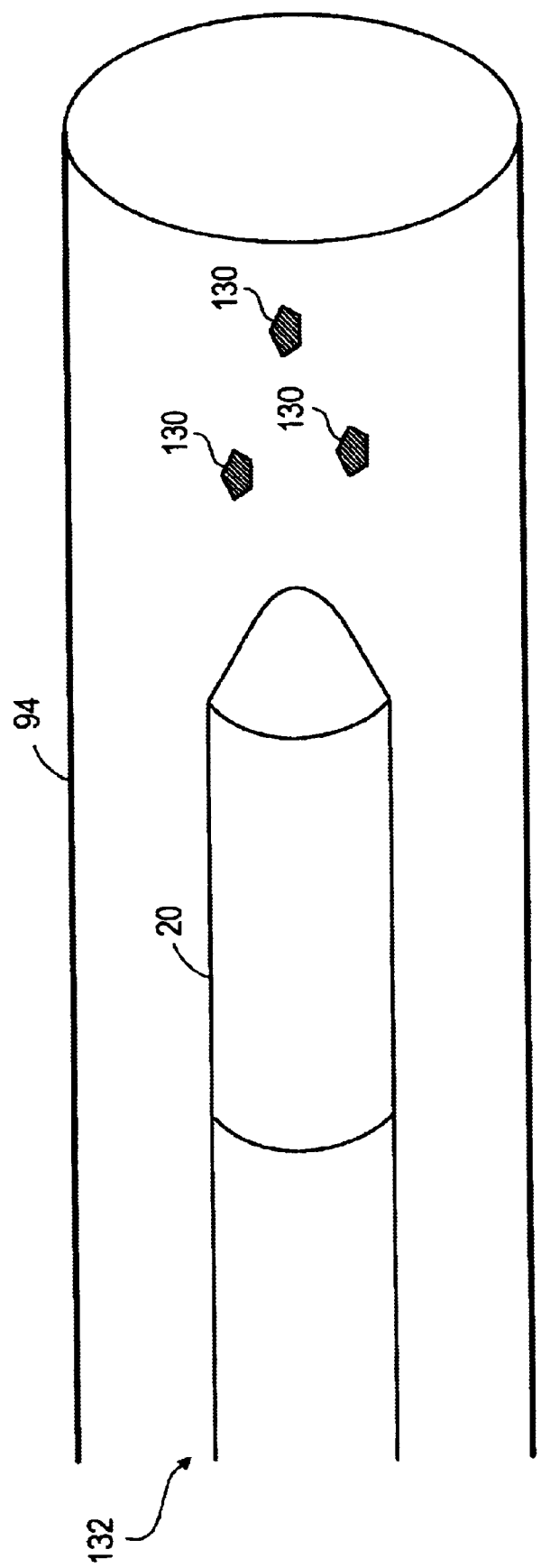
FIG. 11 is an illustration of the balloon electrode structure disposed within a pulmonary vein, wherein all chambers of the balloon electrode structure are in a deflated configuration.
Figure 12:
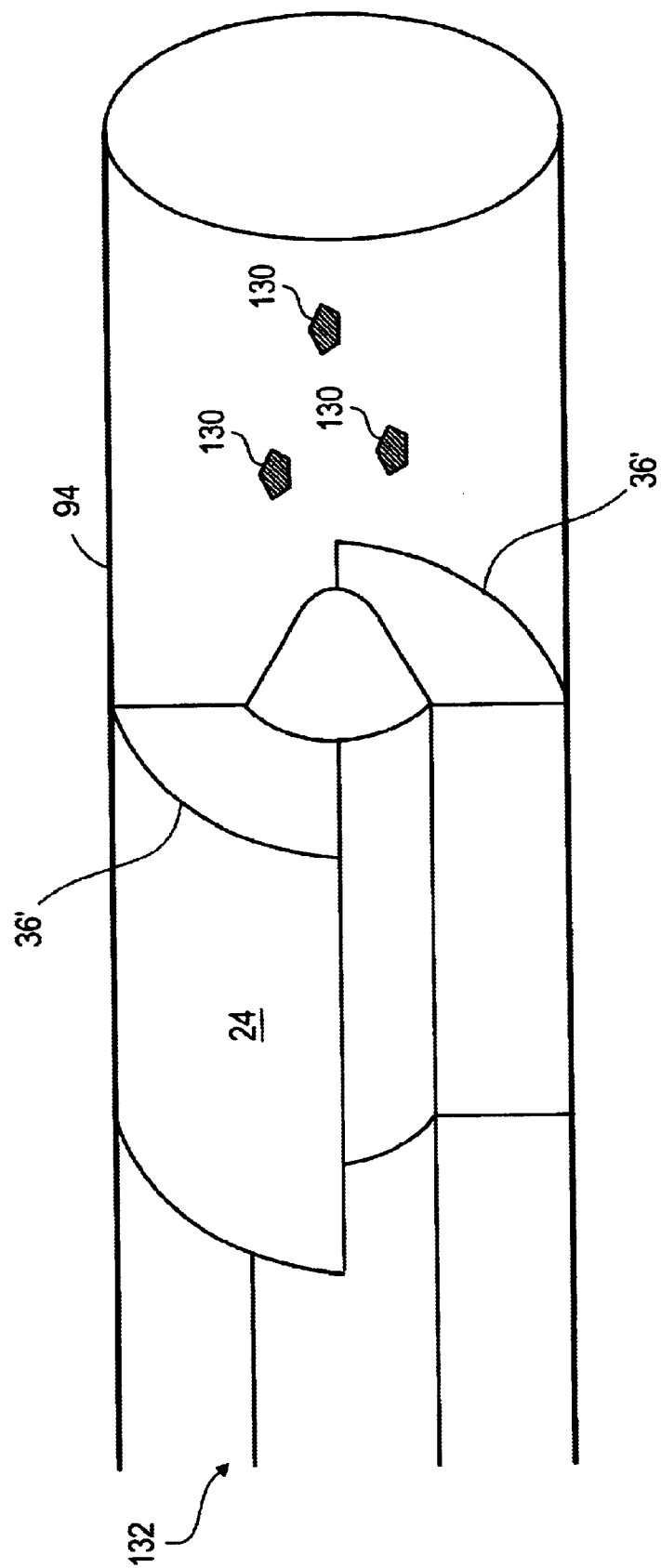
FIG. 12 is an illustration of the balloon electrode structure within a pulmonary vein, wherein two opposing chambers of the balloon electrode structure are in an inflated configuration.

Referring to FIG. 11, in order to isolate focal arrhythmia substrates 130 located in the pulmonary vein 94, the physician situates the balloon electrode structure 20 within a selected tissue region in the interior of the pulmonary vein 94, adjacent to the opening 132 into the left atrium 96. As depicted in FIG. 12, once the balloon electrode structure 20 is properly situated within the pulmonary vein 94, the physician inflates less than all of the inflatable chambers 36—i.e., via the injection of pressurized liquid through the inflation/deflation lumen 62, thereby placing the exterior wall 24 of the chambers 36 into firm contact with the selected tissue region of the pulmonary vein 94.

The physician then causes RF energy to be conveyed from the RF generator 18 to the exterior wall 24 using ionic transport of electrical energy in the manner described above, as governed by the controller 19. The ionic transport of energy causes the RF energy to be transmitted into the tissue of the selected region of the pulmonary vein 94 to a return electrode (not shown), which is preferably an external patch electrode placed upon the patient, thereby forming a unipolar arrangement.

Figure 13:
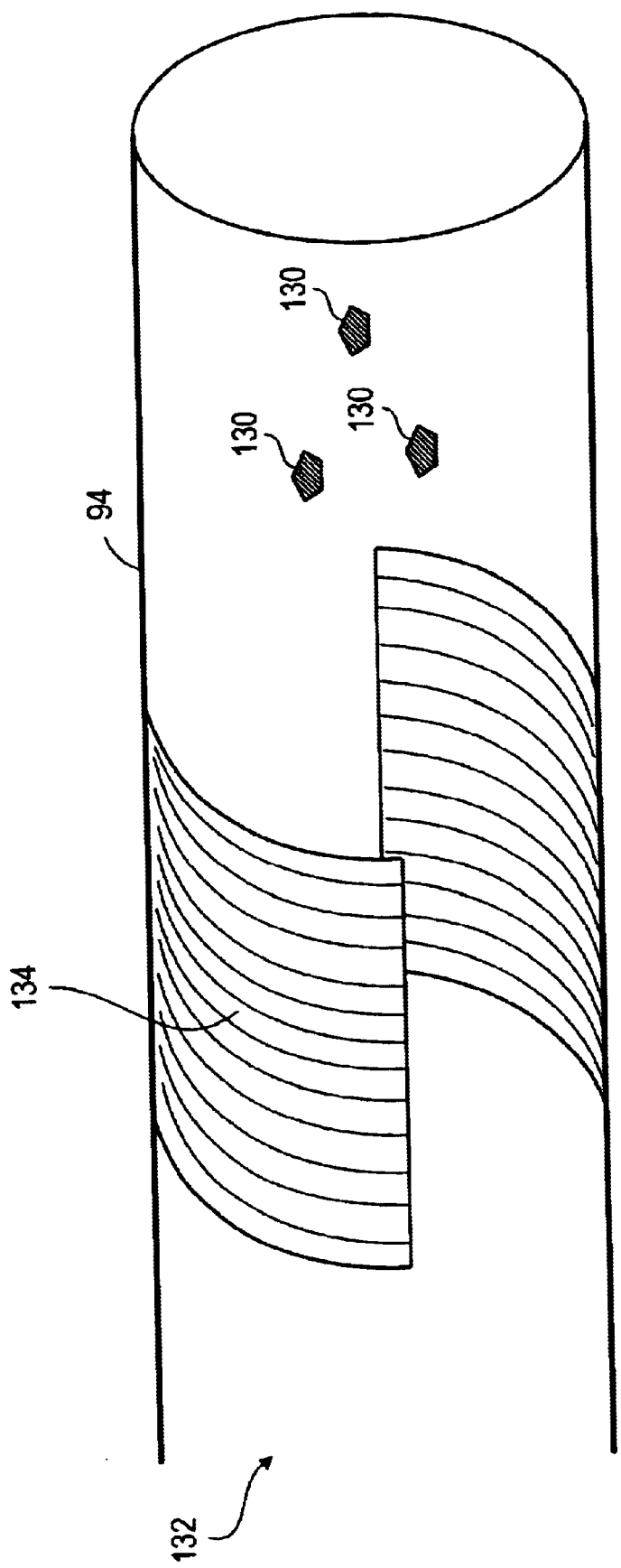
FIG. 13 is an illustration of lesions created within the pulmonary vein by the balloon electrode structure.
Figure 14:
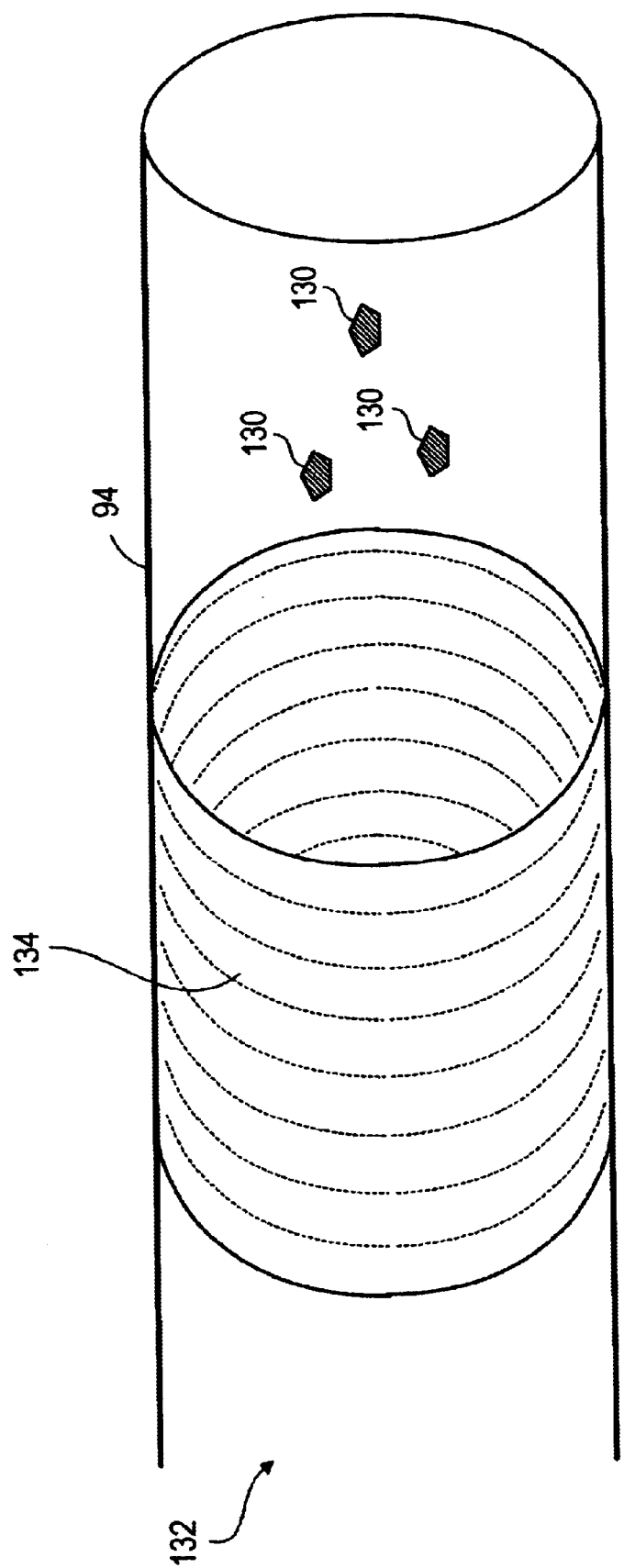
FIG. 14 is an illustration of a continuous lesion created within the pulmonary vein by the balloon electrode structure.

Referring specifically to FIG. 13, the transmitted RF energy creates lesions 134 covering sections of the circumferential region of the pulmonary vein 94 proximate to the exterior walls 24 of the balloon electrode structure 20 were in contact with the tissue. The ablation procedure is then performed on the unablated sections of the circumferential region, whereby, as shown in FIG. 14, the lesion 134 is made to be continuous around the circumferential region and now isolates the focal arrhythmia substrates 130 from the left atrium 96, thus restoring normal myocardial contraction.

Following the ablation process, the physician causes the balloon electrode structure 20 to return to its collapsed geometry—i.e., by removing the liquid inflation medium from the inflatable chambers 36. The physician can then extract the balloon electrode structure 20 from the pulmonary vein 94, after which it can be repositioned inside another pulmonary vein for continued ablation therapy or extracted altogether from the patient.

In another embodiment of the present invention, a multi-chamber stepped balloon electrode structure 145 is shown in FIG. 15A (deflated stated) and FIG. 15B (one chamber inflated state). The stepped balloon electrode structure 145 is segmented such that the diameter varies in size only along its axial length. The stepped balloon electrode structure 145 has a distal end 140, the diameter of which is sizably smaller that the diameter at a proximal end 142 of the balloon structure 145. This allows the user to position the balloon structure 145 at the mouth of a tapered vascular or venous structure, for example, at the ostium of a pulmonary vein.

In addition, the stepped balloon electrode structure 145, in a similar embodiment, could have a stepped portion 144 configured to ablate tissue, and a surface 146 that is configured to not ablate tissue. For example, stepped portion 144 may be microporous, and surface 146 may not be microporous. This feature can allow the user to create narrow lesions in specific sections of the anatomical structure.

The stepped balloon electrode structure of FIGS. 15A and 15B can be employed to isolate focal arrhythmia substrates in vessels such as the pulmonary vein 94 by creating a circumferential lesion either at the base of the vessel or inside of the vessel, depending on which portion of the stepped balloon electrode structure 145 is used.

Specifically, if the stepped balloon electrode structure 145 is being used for ablating the interior of a vessel, the physician can dispose the stepped balloon electrode structure 145 into the interior of the vessel while the structure 145 is in its deflated state. Once inside the vessel, one or more chambers of the stepped balloon electrode structure 145 can be inflated and the physician can transmit ablation energy into the electrode structure for ablation purposes, as described herein. Continuous lesions can be formed using the methods described above.

Figure 16:
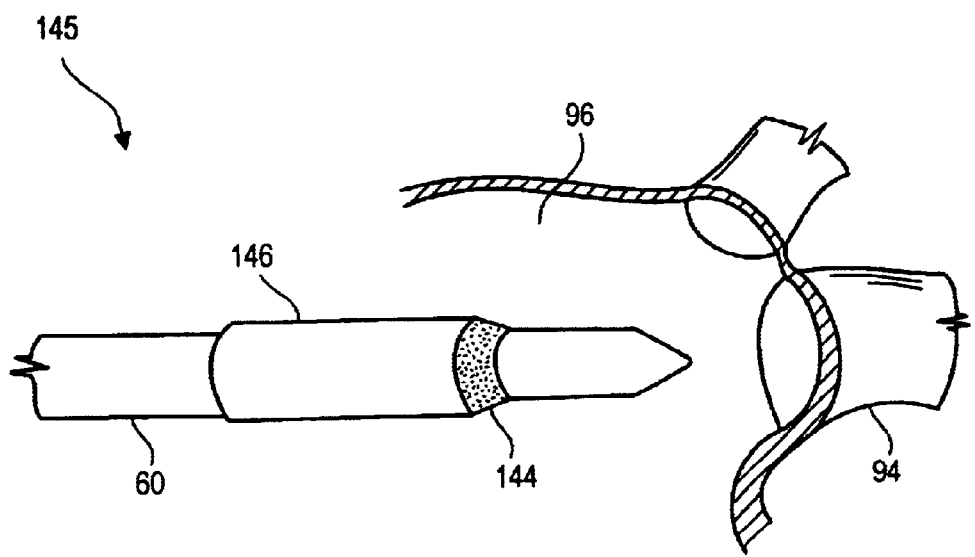
FIG. 16 is an illustration of the stepped balloon electrode structure disposed within the left atrium of the heart, wherein all chambers of the stepped balloon electrode structure are in a deflated configuration.

Referring now to FIGS. 16–20, the stepped balloon electrode structure 145 can be employed to isolate focal arrhythmia substrates in a pulmonary vein 94 by creating a circumferential lesion at the mouth of the pulmonary vein 94. Referring specifically to FIG. 16, the electrode structure 145 is shown disposed within the left atrium 96 of the heart. The electrode structure 145 can be introduced into the left atrium 96 using any of the methods previously described above.

Figure 17:
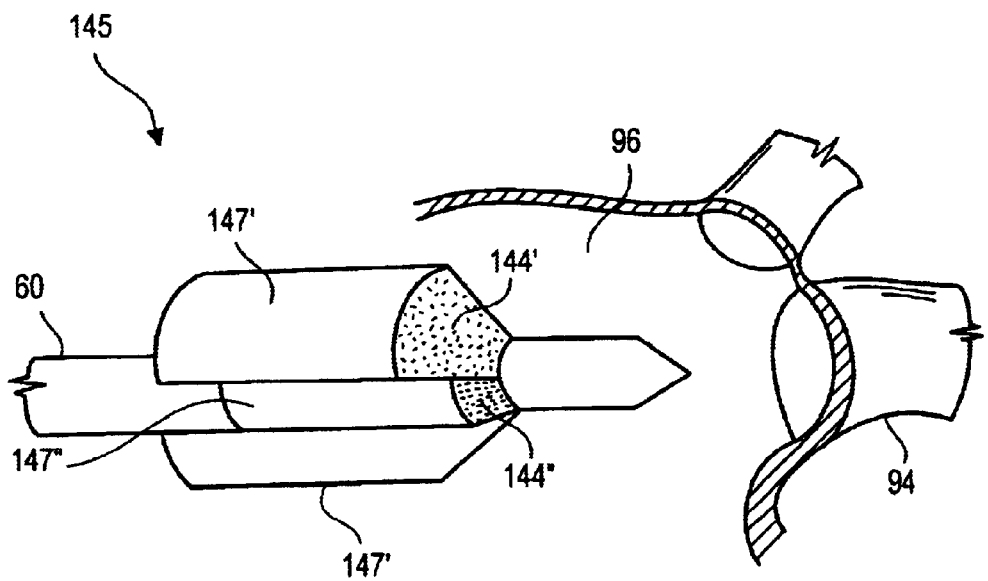
FIG. 17 is an illustration of the stepped balloon electrode structure disposed within the left atrium of the heart, wherein two of the chambers of the stepped balloon electrode structure are in an inflated configuration.

Next, as shown in FIG. 17, a first number of chambers 147' of the electrode structure 145 are then inflated so that the stepped portions 144' are exposed. A second number of chambers 147" and steps 144" are maintained in a deflated state to allow fluids to pass by the electrode structure 145, as will be described below.

Figure 18:
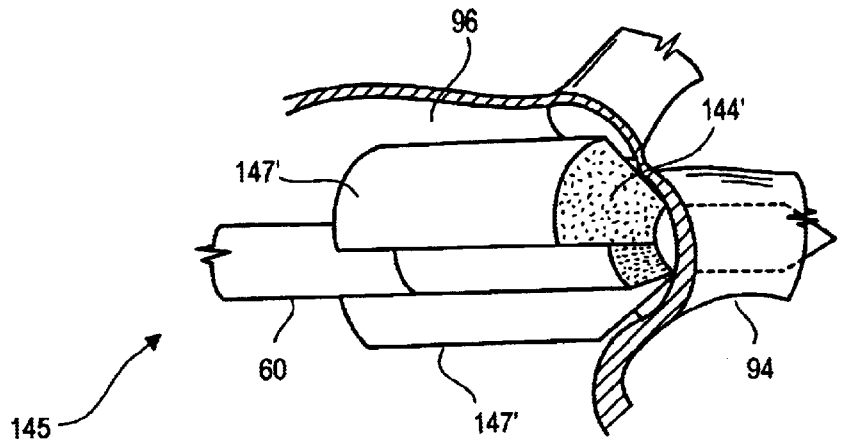
FIG. 18 is an illustration of the stepped balloon electrode structure abutting the mouth of the pulmonary vein.

Turning to FIG. 18, the electrode structure 145 is then guided into the vein 94 until inflated stepped portions 144' butt up against the opening of the vein 94, thereby placing the inflated stepped portions 144' in contact with the opening of the vein 94. As stated above, the deflated chambers 147" and deflated steps 144" of the electrode structure 145 allow fluids to continue flowing past the structure 145.

Figure 19:
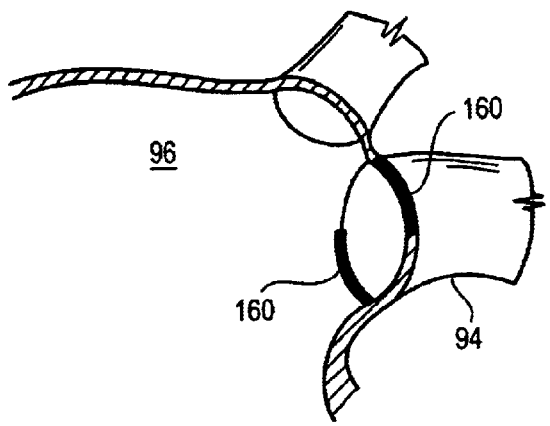
FIG. 19 is an illustration of lesions created at the mouth of the pulmonary vein by the stepped balloon electrode structure.

Next, the physician conveys RF energy to the inflated stepped portions 144', which in turn, transmit RF energy into portions of a circumferential tissue region at the opening of the pulmonary vein 94 to a return electrode (unipolar arrangement) or an adjacent electrode (bipolar arrangement), creating lesions 160 at the opening of the pulmonary vein 94, as shown in FIG. 19.

Figure 20:
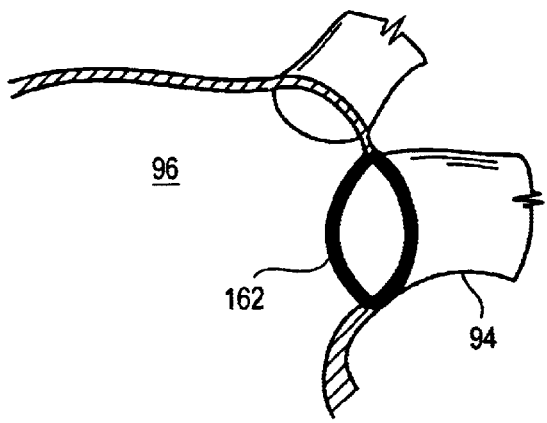
FIG. 20 is an illustration of a continuous lesion created at the mouth of the pulmonary vein by the stepped balloon electrode structure.

Next, the electrode structure is either rotated, or the deflated balloons 144" are inflated and the inflated balloons 144' are deflated. This places inflated stepped portions 144' in contact with unablated portions of the circumferential tissue region at the opening of the pulmonary vein 94, and these portions are then ablated. This technique is continued until a continuous circumferential lesion 162 is created, as shown in FIG. 20, isolating any focal arrhythmia substrates within the pulmonary vein from the left atrium.

Although the above-described preferred methods have been directed to the creation of lesions in pulmonary veins and surrounding openings of the left atrium of the heart, the various systems, methods and apparatus disclosed and described herein can be used to perform tissue ablation procedures in and around the Inferior Vena Cava, the Superior Vena Cava, left and right ventricles, the free wall of the atria, and the Sinus Coronary, which are located in the right atrium, as well as other vessels and cavities within the body, e.g., the esophagus in treating gastroesophageal reflux disease.

While preferred embodiments have been shown and described, it will be apparent to one of ordinary skill in the art that numerous alterations may be made without departing from the spirit or scope of the invention. Thus, the invention is not to be limited except in accordance with the following claims.

What is claimed is:

1. An ablation catheter, comprising:
an elongate catheter body, comprising:
an inner shaft having an inner shaft lumen;
a stiffening mandrel disposed within the inner shaft lumen;
and an outer shaft having an outer shaft lumen, wherein the inner shaft is disposed within the outer shaft lumen; and
an electrode structure mounted on a distal end of the catheter body, the electrode structure comprising a plurality of radially disposed inflatable chambers.

2. The ablation catheter of claim 1, wherein the electrode structure comprises an exterior wall peripherally surrounding an interior area of each of the inflatable chambers.

3. The ablation catheter of claim 2, wherein each inflatable chamber comprises a distinct wall, and the exterior wall is formed by an aggregate of the plurality of distinct walls.

4. The ablation catheter of claim 2, wherein the exterior wall is common to the plurality of inflatable chambers and adjacent inflatable chambers are separated by respective ribs.

5. The ablation catheter of claim 2, wherein the exterior wall is ablative.

6. The ablation catheter of claim 5, wherein the ablative exterior wall comprises a microporous material.

7. The ablation catheter of claim 5, wherein the ablative exterior wall comprises an electrically conductive material.

8. The ablation catheter of claim 1, wherein the electrode structure is capable of delivering RF ablation energy.

9. The ablation catheter of claim 1, wherein the plurality of inflatable chambers comprises four inflatable chambers.

10. The ablation catheter of claim 1, wherein the outer shaft comprises a plurality of inflation lumens in communication with the interior regions of the inflatable chambers.

11. The ablation catheter of claim 1, wherein the inner shaft comprises a plurality of lumens and a plurality of electrical leads for delivery of ablation energy to the electrode structure, wherein the plurality of electrical leads are respectively disposed within the plurality of lumens.

12. The ablation catheter of claim 1, further comprising a handle mounted on the proximal end of the catheter body.

13. The ablation catheter of claim 1, further comprising a radio-opaque marker disposed on the distal end of the catheter body.

14. The ablation catheter of claim 1, wherein, when inflated, the electrode structure has a proximal portion having a diameter that is greater than the diameter of a pulmonary vein ostium, and a distal portion having a diameter that is less than the diameter of the pulmonary vein ostium.

15. The ablation catheter of claim 1, wherein the electrode structure is cylindrical when the plurality of chambers is inflated.

16. The ablation catheter of claim 1, wherein the chambers are independently inflatable.

17. An ablation catheter, comprising:
an elongate catheter body; and
an electrode structure mounted on a distal end of the catheter body, the electrode structure comprising a plurality of radially disposed inflatable balloons, each of the balloons comprising a distinct exterior ablative wall.

18. The ablation catheter of claim 17, wherein the electrode structure comprises an exterior wall peripherally surrounding an interior area of the inflatable balloons, the exterior wall being formed by an aggregate of the plurality of distinct walls.

19. The ablation catheter of claim 17, wherein the electrode structure is capable of delivering RF ablation energy.

20. The ablation catheter of claim 17, wherein the distinct ablative walls comprise microporous material.

21. The ablation catheter of claim 17, wherein the distinct ablative walls comprise electrically conductive material.

22. The ablation catheter of claim 17, wherein the plurality of inflatable balloons comprises four inflatable balloons.

23. The ablation catheter of claim 17, wherein the elongate catheter body, comprises:
an inner shaft having an inner shaft lumen;
a stiffening mandrel disposed within the inner shaft lumen; and
an outer shaft having an outer shaft lumen, wherein the inner shaft is disposed within the outer shaft lumen.

24. The ablation catheter of claim 23, wherein the outer shaft comprises a plurality of inflation lumens in communication with the interior regions of the inflatable balloons.

25. The ablation catheter of claim 23, wherein the inner shaft comprises a plurality of lumens and a plurality of electrical leads for delivery of ablation energy to the electrode structure, wherein the plurality of electrical leads are respectively disposed within the plurality of lumens.

26. The ablation catheter of claim 17, further comprising a handle mounted on the proximal end of the catheter body.

27. The ablation catheter of claim 17, further comprising a radio-opaque marker disposed on the distal end of the catheter body.

28. The ablation catheter of claim 17, wherein, when inflated, the electrode structure has a proximal portion having a diameter that is greater than the diameter of a pulmonary vein ostium, and a distal portion having a diameter that is less than the diameter of the pulmonary vein ostium.

29. The ablation catheter of claim 17, wherein the electrode structure is cylindrical when the plurality of balloons is inflated.

30. The ablation catheter of claim 17, wherein the balloons are independently inflatable.

31. An ablation catheter, comprising:
an elongate catheter body; and
an electrode structure mounted on a distal end of the catheter body, the electrode structure comprising a plurality of inflatable chambers radially disposed about a lumen, the elongate catheter body mounted within the lumen.

32. The ablation catheter of claim 31, wherein the electrode structure comprises an exterior wall peripherally surrounding an interior area of the inflatable chambers.

33. The ablation catheter of claim 32, wherein each inflatable chamber comprises a distinct wall, and the exterior wall is formed by an aggregate of the plurality of distinct walls.

34. The ablation catheter of claim 32, wherein the exterior wall is common to the plurality of inflatable chambers and adjacent inflatable chambers are separated by respective ribs.

35. The ablation catheter of claim 32, wherein the exterior wall is ablative.

36. The ablation catheter of claim 35, wherein the ablative exterior wall comprises microporous material.

37. The ablation catheter of claim 35, wherein the ablative exterior wall comprises electrically conductive material.

38. The ablation catheter of claim 31, wherein the electrode structure is capable of delivering RF ablation energy.

39. The ablation catheter of claim 31, wherein the plurality of inflatable chambers comprises four inflatable balloons.

40. The ablation catheter of claim 31, wherein the elongate catheter body, comprises:

an inner shaft having an inner shaft lumen;

a stiffening mandrel disposed within the inner shaft lumen; and an outer shaft having an outer shaft lumen, wherein the inner shaft is disposed within the outer shaft lumen.

41. The ablation catheter of claim 40, wherein the outer shaft comprises a plurality of inflation lumens in communication with the interior regions of the inflatable chambers.

42. The ablation catheter of claim 40, wherein the inner shaft comprises a plurality of lumens and a plurality of electrical leads for delivery of ablation energy to the electrode structure, wherein the plurality of electrical leads are respectively disposed within the plurality of lumens.

43. The ablation catheter of claim 40, wherein the inner shaft is mounted within the lumen of the electrode structure.

44. The ablation catheter of claim 31, further comprising a handle mounted on the proximal end of the catheter body.

45. The ablation catheter of claim 31, further comprising a radio-opaque marker disposed on the distal end of the catheter body.

46. The ablation catheter of claim 31, wherein, when inflated, the electrode structure has a proximal portion having a diameter that is greater than the diameter of a pulmonary vein ostium, and a distal portion having a diameter that is less than the diameter of the pulmonary vein ostium.

47. The ablation catheter of claim 31, wherein the electrode structure is cylindrical when the plurality of chambers is inflated.

48. The ablation catheter of claim 31, wherein the chambers are independently inflatable.

* * * * *

UNITED STATES PATENT AND TRADEMARK OFFICE
CERTIFICATE OF CORRECTION

PATENT NO. : 6,656,174 B1
DATED : December 2, 2003
INVENTOR(S) : Anant V. Hegde, Steven L. Olson and David K. Swanson It is certified that error appears in the above-identified patent and that said Letters Patent is hereby corrected as shown below:

<u>Title page, Item [54] and Column 1, lines 1 and 2,</u>
Delete "DEVICES AND METHODS FOR CREATING LESIONS IN BLOOD VESSELS WITHOUT OBSTRUCTING BLOOD FLOW" and insert therefore
-- ABLATION CATHETER WITH RADIALLY DISPOSED INFLATABLE CHAMBERS --

Signed and Sealed this

Thirteenth Day of April, 2004

JON W. DUDAS
*Acting Director of the United States Patent and Trademark Office*